US009908140B2

(12) United States Patent
Arwatz et al.

(10) Patent No.: US 9,908,140 B2
(45) Date of Patent: *Mar. 6, 2018

(54) ELECTROMECHANICAL SYSTEM FOR DISPENSING A COMPOSITION

(71) Applicants: Gilad Arwatz, Princeton, NJ (US); Carla Bahri, Plainsboro, NJ (US)

(72) Inventors: Gilad Arwatz, Princeton, NJ (US); Carla Bahri, Plainsboro, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/899,725

(22) PCT Filed: Jun. 19, 2014

(86) PCT No.: PCT/IL2014/050560
§ 371 (c)(1),
(2) Date: Dec. 18, 2015

(87) PCT Pub. No.: WO2014/203260
PCT Pub. Date: Dec. 24, 2014

(65) Prior Publication Data
US 2016/0151803 A1    Jun. 2, 2016

Related U.S. Application Data

(63) Continuation-in-part of application No. 13/921,543, filed on Jun. 19, 2013, now Pat. No. 9,210,985.
(Continued)

(51) Int. Cl.
*B43K 1/06* (2006.01)
*B05C 17/01* (2006.01)
(Continued)

(52) U.S. Cl.
CPC ....... *B05C 17/0103* (2013.01); *A61M 35/003* (2013.01); *B65D 83/0011* (2013.01); *A45D 34/04* (2013.01); *A45D 2200/055* (2013.01)

(58) Field of Classification Search
CPC ............ A45D 40/205; A45D 2040/208; B65D 83/0011
(Continued)

(56) References Cited

U.S. PATENT DOCUMENTS 5,538,161 A    7/1996    Koehler et al.
5,753,212 A    5/1998    Pescatore et al.
(Continued)

FOREIGN PATENT DOCUMENTS

WO    2011/047408 A1    4/2011
WO    2012/013542       2/2012
(Continued)

OTHER PUBLICATIONS

European Search Report dated Oct. 25, 2016, which issued during the prosecution of Applicant's European App No. 14814028.8.
(Continued)

*Primary Examiner* — Jennifer C Chiang
(74) *Attorney, Agent, or Firm* — Sughrue Mion, PLLC

(57) ABSTRACT

Apparatus is described for use with a container (102) for dispensing a composition (112), the container including a movable platform (106). The apparatus includes a container holder (101), which includes: an upper portion (116), which includes one or more user input elements (104); and a lower portion, including a driving unit (201, 3001) and a power source (205, 3008). The power source (205, 3008) is operative to drive the driving unit (201, 3001) to move the movable platform (106) of the container (102), in response to actuation of the one or more user input elements (104). Other applications are also described.

44 Claims, 23 Drawing Sheets

Related U.S. Application Data

(60) Provisional application No. 61/863,979, filed on Aug. 9, 2013, provisional application No. 61/875,032, filed on Sep. 7, 2013.

(51) Int. Cl.
*A61M 35/00* (2006.01)
*B65D 83/00* (2006.01)
*A45D 34/04* (2006.01)

(58) Field of Classification Search
USPC ..................................... 401/55, 68, 81, 101
See application file for complete search history.

(56) References Cited

U.S. PATENT DOCUMENTS

| | | |
|---|---|---|
| 5,862,844 A | 1/1999 | Perrin |
| 6,269,982 B1 | 8/2001 | Kreiseder et al. |
| 6,708,060 B1 | 3/2004 | Avrahami et al. |
| 7,629,757 B2 | 12/2009 | Murphy et al. |
| 8,235,615 B2 | 8/2012 | Yarlagadda |
| 8,393,338 B2 | 3/2013 | Wyatt et al. |
| 8,393,813 B2 | 3/2013 | Yarlagadda |
| 9,210,985 B2 | 12/2015 | Arwatz et al. |
| 2008/0025785 A1 | 1/2008 | Ma et al. |
| 2009/0308887 A1 | 12/2009 | Woo et al. |
| 2011/0150555 A1 | 6/2011 | Yarlagadda |
| 2011/0190672 A1 | 8/2011 | Apodaca et al. |
| 2011/0259974 A1 | 10/2011 | Cooper et al. |
| 2012/0121309 A1 | 5/2012 | Liu |
| 2014/0174464 A1 | 6/2014 | Drugeon et al. |
| 2014/0376986 A1 | 12/2014 | Arwatz et al. |

FOREIGN PATENT DOCUMENTS

| | | |
|---|---|---|
| WO | 2012/081011 | 6/2012 |
| WO | 2012/082138 | 6/2012 |
| WO | 2014/203260 | 12/2014 |

OTHER PUBLICATIONS

International Search Report of PCT/IL2014/050560 dated Jan. 29, 2015.
An International Preliminary Report on Patentability dated Dec. 22, 2015, which issued during the prosecution of Applicant's PCT/IL2014/050560.
An Office Action dated Jun. 10, 2015, which issued during the prosecution of U.S. Appl. No. 13/921,543.
Notice of Allowance dated Sep. 23, 2015, which issued during the prosecution of U.S. Appl. No. 13/921,543.
U.S. Appl. No. 61/875,032, filed Sep. 6, 2013.
U.S. Appl. No. 61/863,979, filed Aug. 9, 2013.

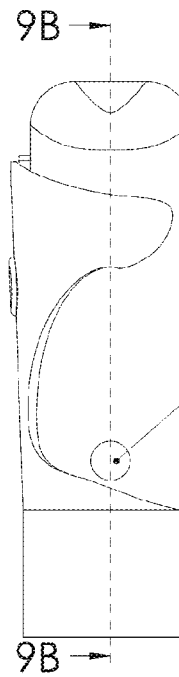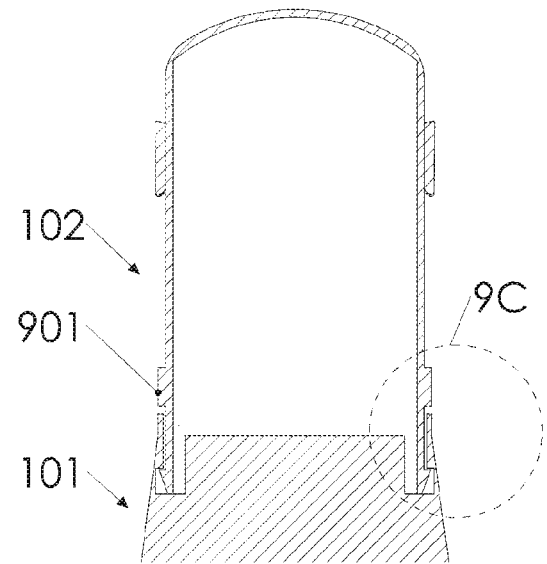
FIG. 9A    FIG. 9B
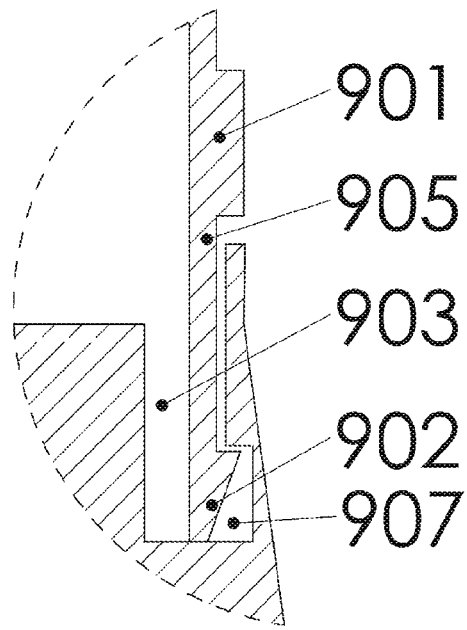
FIG. 9C

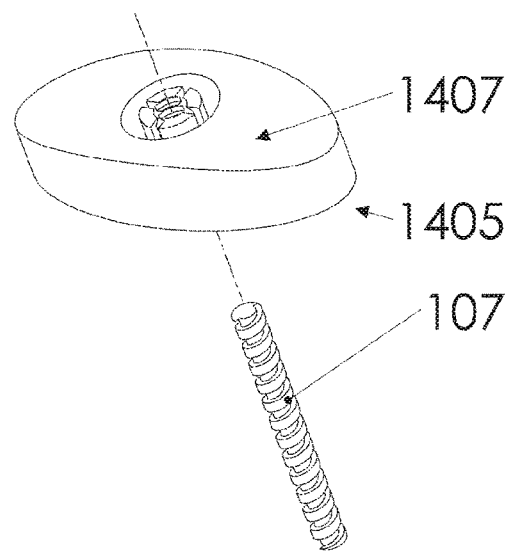
FIG. 15
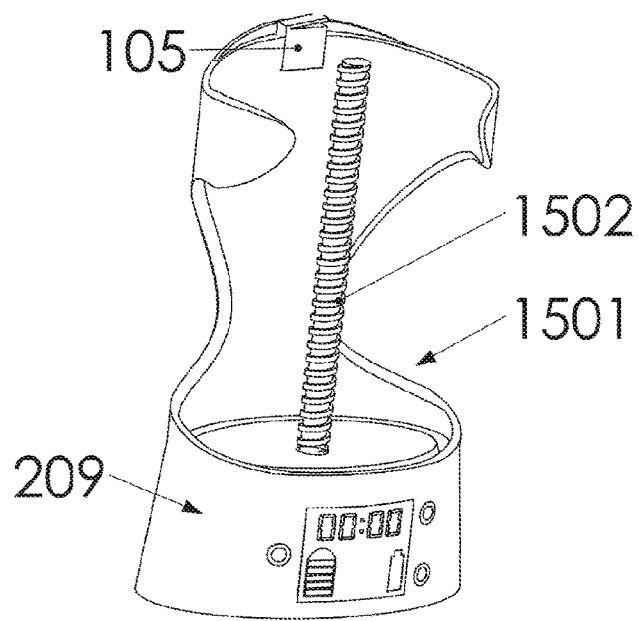 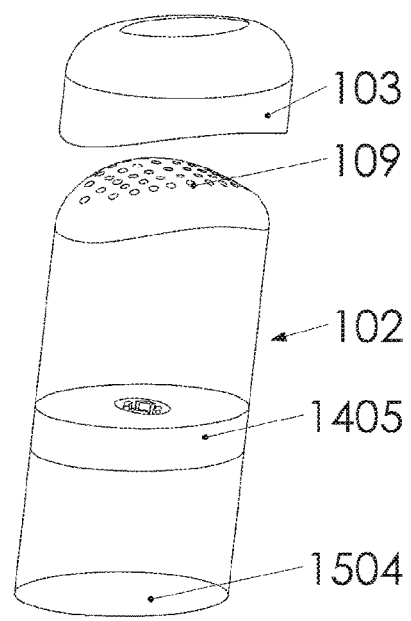
FIG. 16A  FIG. 16B

ELECTROMECHANICAL SYSTEM FOR DISPENSING A COMPOSITION

CROSS-REFERENCE TO RELATED APPLICATIONS

The present application is a U.S. National Stage of International Application No. PCT/IL2014/050560, filed Jun. 19, 2014, which claims the benefit of and is a continuation-in-part of U.S. patent application Ser. No. 13/921,543, filed Jun. 19, 2013, now U.S. Pat. No. 9,210,985, and claims the benefit of (a) U.S. Provisional Application No. 61/863,979, filed Aug. 9, 2013, and (b) U.S. Provisional Application No. 61/875,032, filed Sep. 7, 2013. Each of the above-referenced applications is incorporated herein by reference.

TECHNICAL FIELD

The present invention relates to an electromechanical system for dispensing a composition.

BACKGROUND OF THE INVENTION

Deodorant/antiperspirant apparatus traditionally comprises a container including the composition, which can be either a viscous fluid (gel) or a solid stick, a threaded shaft coupled to a turnbuckle, and a platform. The user turns the turnbuckle, which rotates the threaded shaft, and moves the platform up which in turn pushes the deodorant/antiperspirant out of the container. Although the shapes and design may vary, the basic operation mechanism is almost identical for all present apparatus in the market.

The existing and commonly used manual mechanism for dispensing deodorant/antiperspirant suffers from several issues. The manual apparatus requires the use of two hands in order to dispense the composition; one hand is holding the apparatus while the other hand is rotating the turnbuckle. As a consequence, the user has to move the apparatus to the armpit after the composition has been extruded. As a result, the clothes are often stained due to the contact of the deodorant/antiperspirant with the fabric.

Another issue that may be addressed is the amount of dispensed deodorant/antiperspirant. In most existing apparatus, the user has to look at the composition as it is being dispensed when the buckle turns in order to estimate the amount needed. As a consequence, the user dispenses a different amount each time. In order to address this issue, in some apparatus, the turnbuckle clicks upon rotation. Since the clicks correspond to a certain angular rotation, by counting the clicks, the user can control the dispensed amount in a repeatable manner. However, this requires the user to learn and memorize the number of clicks needed.

In addition, there are no guidelines regarding the appropriate amount to be used and therefore the user often dispenses more or less than needed. Hence, there is a need to introduce an automatic mechanism that fixes the amount needed allowing the user to dispense the same amount in every application.

The existing dispensing apparatus for deodorant/antiperspirant comprises the composition and the lifting mechanism as one entity making it complex to manufacture and assemble and relatively expensive. In addition the user usually throws away the entire device after the composition has all been dispensed. Therefore, there is a desire for making the disposable part of the apparatus simpler.

A problem for solid stick composition is that the user cannot determine the remaining amount of composition and therefore, typically the last piece of the stick suddenly falls off during use, leaving the user with no deodorant. Therefore, there is a desire for a way to indicate to the user that the stick is about to reach its end.

Some users tend to forget when was the last time they applied the deodorant/antiperspirant and hence apply the composition twice or more, consecutively, while others may forget to apply the composition. Therefore, there is a desire for apparatus that will have means to indicate when and if the composition has been applied.

All of the issues described above can be applied to other fields and other types of compositions, for example a skin-care composition, a composition including a pharmaceutical composition, a cosmetic composition, and an ultrasound gel composition. Existing dispensers for many such compositions lack a way to accurately predetermine the amount of the composition that is dispensed. They also lack a way to effectively infuse the composition into the skin and therefore there is a desire for a dispenser comprising a specific vibration element, to enhance infusion of the composition into the skin. In many pharmaceutical applications, the composition includes ingredients that require accurate dosage, proper handling and minimal hand contact. Therefore, there is a desire for a dispenser with accurate dosage and a means to dispense the composition without direct contact. In addition, some pharmaceutical products are currently using conventional deodorant/antiperspirant dispensers described above and therefore suffer from most of the problems previously discussed. Ultrasound gels are typically applied by squeezing a bottle, which in many cases dispenses an excessive amount, resulting in inconvenience and significant waste. Therefore, there is a desire to provide an ultrasound gel dispenser that minimizes waste and prevents inconvenience.

SUMMARY OF THE INVENTION

Applications of the present invention are related to a dispensing apparatus for deodorant/antiperspirant wherein the composition comprises either a viscous or a solid stick composition. The composition may alternatively or additionally comprise a skin-care composition, a composition including a pharmaceutical composition, a cosmetic composition, or an ultrasound gel composition. The dispensing apparatus comprises a container holder comprising one or more user input elements, a driving unit, a power source and an optional electronic circuit. The apparatus also comprises a container that contains the composition and a movable platform configured such that movement of the platform dispenses the composition from the container. A threaded shaft moves the platform and in some embodiments it is an integral part of either the container or the container holder. In embodiments where the container comprises a shaft, rotation of the shaft within the container does not move the platform and the user cannot use the container when it is not coupled to the container holder. The above also applies to embodiments in which the container holder comprises a shaft and the container comprises the platform; the container cannot be used without the container holder.

In embodiments where the container and the container holder are not fixedly coupled, the consumer typically buys one container holder and reuses it with a container. In this case, the container and the container holder, being two separate entities, are attached using a user-activatable release mechanism operative to release the container from the container holder, allowing the user to replace the container while keeping the container holder. The container as packaged for sale typically comprises a composition, a movable platform and it may or may not comprise a shaft. Since the container does not have means (e.g. turn-buckle) to rotate a shaft and thus lift the platform, the container is cheaper and simpler to manufacture with fewer parts. In other embodiments, the apparatus may comprise one inseparable unit where the container holder is fixedly coupled to the container. In this case, the consumer may refill the apparatus when the composition is all dispensed or alternatively may replace it with a new apparatus.

An element in operating the apparatus is typically pressing a user input element to activate the driving unit and dispense the composition. Typically, the user input element is located roughly at mid-height of the container. Since the container and container holder can be separate entities and the container may be disposable, having the user input element on the container is for some applications not desirable. To address this, the container holder is shaped in a way that allows the user input element to be located in a convenient location, allowing the user easy operation while holding the apparatus in one hand. Specifically, to serve this purpose, the container holder may be extruded upwardly along the container. In addition, the container holder may include a container-coupling upper portion comprising one or more grips, which are configured to hold the upper portion of the container.

In some embodiments, the container holder may comprise a coupling-detection element, configured to detect coupling of the container holder to the container. In other embodiments, the container and the container holder may comprise complementary shapes, which may serve as a locking/release mechanism that couples the container to the container holder. The features listed above provide that a matching container and container holder are used. A non-matching container and container holder do not couple properly.

The driving unit may be configured to move the movable platform a predetermined distance in response to actuation of the one or more user input elements, in order to control the amount of composition dispensed in one cycle of operation. This is typically accomplished by either setting the angular rotations performed by the driving unit or the time it takes to dispense the desired dose.

Optionally the container holder further comprises a user input element, which is configured to disable functioning of the driving unit. This user input element may comprise a switch, configured to disable functioning of the driving unit when a cap of the container is disposed on the container, in order to extend battery life and prevent accidental operation. A design of the container holder also allows for this switch to be positioned such that it is pressed when the cap is closed.

Optionally, the container comprises a platform and a shaft. One end of the shaft is coupled (e.g., threadedly engaged) to the platform and the other end has a shape that couples to the driving unit in the container holder. In other embodiments the container holder comprises a threaded shaft fixedly coupled to the driving unit, the threaded shaft being insertable into the movable platform of the container. In this case, the container comprises a platform but not a shaft. In this embodiment, the platform is modified to allow the threaded shaft to be inserted into the platform in one direction without rotation of the threaded shaft with respect to the movable platform. Once the shaft is in place, the platform can be lifted by rotation of the shaft, as with a typical platform. As previously mentioned, the conventional deodorant dispensers comprise a turn-buckle to facilitate rotation of the shaft in order to lift the platform. Applications of the present invention are different since there is no turn-buckle and lifting the platform is done by coupling the container to the container holder and operating the driving unit.

Once the container is coupled to the container holder (e.g., by the user), the container holder is typically an integral part of the apparatus and it is not a separate entity during use. Typically, the size of the apparatus when the container is coupled to the container holder is similar to the size of conventional deodorant dispensers. In other non-antiperspirant/deodorant applications, the size of the dispenser may be similar to the size of related existing dispensers or may be suitable for dispensing the composition in use.

In some embodiments, the apparatus comprises a mechanism that automatically dispenses the composition out of the container when the user places the apparatus near or on the desired location of application.

In other embodiments, the container may comprise a power source (e.g., one or more batteries), which upon coupling to the container holder provide power to the driving unit. This feature can eliminate the need for the user to replace batteries since upon completion of the composition the user loads a new container that comprises new batteries. In this embodiment, the container holder has no power source to drive the driving unit and therefore cannot be used with a container without a power source.

In some embodiments, where the composition comprises a solid stick, the apparatus may comprise one fixedly coupled unit, where the refill comprises the solid stick with no container. In addition, in some embodiments, the platform may be configured to move up or down to deliver and retract the composition, respectively. In other embodiments, a level indication sensor may be included. The indicator may indicate the remaining amount of composition or may indicate that the composition is about to end.

In other embodiments, the apparatus comprises a light source that may comprise an LED or any other light source. The light source may be operated when the user removes the cap, for example and it may serve to illuminate the composition and clearly show the remaining amount of the composition. The light can alternatively or additionally be used to signal the user that the cap is properly placed.

In some embodiments, the apparatus may include a display showing the time the composition has last been applied, the time elapsed since the last use, the remaining amount of composition, the remaining number of applications, and/or remaining power.

In other embodiments, the apparatus is for use with a container that contains a composition, such as a skin-care and/or cosmetic composition such as an anti-aging cream, an eye cream, a cleanser, a moisturizing cream, a concealer, a liquid foundation, an acne treatment, a body lotion, a lip gloss and many others. The apparatus may comprise a vibration element configured to be activated upon actuation of the one or more user input elements, to enhance composition infusion to the skin and/or to give a pleasurable feeling to the user. In addition, the apparatus may comprise a way to dispense a predetermined amount of composition, which offers an advantage for the above-listed compositions, due to their relatively high price and due to the fact that only a small amount is often required.

In some embodiments, the composition comprises a pharmaceutical composition such as a hormone containing composition such as testosterone, or a hormone such as estrogen, progesterone, dehydroepiandrosterone (DHEA), cortisone and others. In these applications, the predetermined amount is of therapeutic importance, and the apparatus typically includes elements described herein for delivering the predetermined amount of the composition. The apparatus typically comprises a user-activatable release mechanism operative to release the container from the container holder, which allows for disposal of the container containing the composition when needed. In addition, the user typically does not directly handle the composition. The upper portion of the container may be shaped to fit any suitable skin application area.

In other embodiments, the composition comprises a pharmaceutical composition such as diclofenac (Voltaren™) gel; methyl salicylate, menthol, camphor, and/or triethanolamine salicylate (Bengay™ or Icy Hot™, Mebo™, a pressure sore treatment, or another composition. In these applications, a large application area is sometimes required. In many applications, the treatment is performed by another person (not the patient). The apparatus is typically used without direct handling of the composition and therefore prevents the other person from coming into contact with the composition in use. Here, the upper portion of the container may be shaped to fit any suitable application area and size.

In other embodiments, the apparatus may be used with pharmaceutical or skin-care composition for localized treatments such as acne, scars, age spots, sun spots, and others. In these embodiments, the apparatus is shaped to facilitate accurate dispensing of a small predetermined amount of the composition.

There is therefore provided, in accordance with some applications of the present invention, apparatus for use with a container for dispensing a composition including at least one composition selected from the group consisting of: a deodorant and an antiperspirant, the container including a movable platform, the apparatus including: a container holder including: an upper portion, which includes one or more user input elements; and a lower portion including a driving unit and a power source, the power source being operative to drive the driving unit to move the movable platform of the container, in response to actuation of the one or more user input elements.

In some applications, the container holder includes a coupling-detection element, configured to detect coupling of the container holder to the container. In some applications, the container holder includes a coupling-detection element, configured to detect coupling of the container holder to the container, and the coupling-detection element is configured to detect a predefined shape characteristic of a portion of the container, and to inhibit driving of the driving unit in the absence of a detection of the predefined shape. In some applications, the coupling-detection element is configured to detect the predefined shape characteristic by assessing an electrical current that is changed by coupling of the portion of the container having the predefined shape characteristic to the container holder. In some applications, the container holder includes a coupling-detection element, configured to detect coupling of the container holder to the container, and the coupling-detection element is configured to detect at least one parameter selected from the group consisting of: electrical contact of the coupling-detection element with a conductive portion of the container, magnetic coupling of a portion of the coupling-detection element with a corresponding portion of the container, and a level of reflection from a portion of the container.

In some applications, the one or more user input elements include one or more user push-buttons. In some applications, the one or more user input elements are disposed on an upper 75% of the container holder. In some applications, the one or more user input elements are disposed on an upper 50% of the container holder. In some applications, the one or more user input elements are disposed on an upper 40% of the container holder. In some applications, the one or more user input elements are configured to be placed in a vicinity of an upper 75% of the container, when the container is coupled to the container holder. In some applications, the one or more user input elements are configured to be placed in a vicinity of an upper 50% of the container, when the container is coupled to the container holder.

In some applications, the user input elements include electronic user input elements, and the driving unit includes an electromechanical driving unit.

In some applications, the user input elements include non-electronic user input elements, and the driving unit includes a non-electromechanical driving unit. In some applications, the user input elements include mechanical user input elements, and the driving unit includes a spring-based driving unit. In some applications, the container holder includes a knob configured to facilitate winding of the spring.

In some applications, the container holder includes a user-activatable release mechanism operative to release the container from the container holder. In some applications, the user-activatable release mechanism is disposed on the lower portion of the container holder. In some applications, the user-activatable release mechanism is disposed on the upper portion of the container holder. In some applications, the user-activatable release mechanism includes an energy-storage element, which is configured to store energy by deformation thereof, upon initial coupling of the container to the container holder, and which is configured to release the stored energy during the coupling of the container to the container holder, prior to actuation of the user-activatable release mechanism. In some applications, the container holder is operative to become locked to the container by means of the release of the stored energy during the coupling of the container to the container holder, prior to actuation of the user-activatable release mechanism.

In some applications, the upper portion is shaped to define a container-coupling upper portion, configured to couple the upper portion of the holder to sides of the container. In some applications, the container-coupling upper portion includes one or more grips which are configured to hold an upper portion of the container. In some applications, the container-coupling upper portion includes exactly two wings which are configured to hold an upper portion of the container. In some applications, the two wings are configured to simultaneously apply a pressing force to the container. In some applications, the upper portion is shaped to define a spine, extending up from the lower portion.

In some applications, the upper portion is shaped to define a spine, extending up from the lower portion, and the upper portion is shaped to define at least one shape selected from the group consisting of: one or more grips extending from the spine, the one or more grips being configured to prevent the spine from bending by holding the spine in contact with the container, and a closed shape having an opening therein, which closed shape is configured to completely surround at least a portion of the container.

In some applications, the driving unit is configured to move the movable platform a predetermined distance in response to actuation of the one or more user input elements. In some applications, the apparatus further includes a portion-quantity input element, configured to receive an indication of a desired quantity of the composition, and the apparatus is operative to set the predetermined distance based on the indication of the desired quantity. In some applications, the predetermined distance is a fixed distance, and the driving unit is configured to move the movable platform the fixed distance, in response to actuation of the one or more user input elements.

In some applications, the apparatus further includes a second user input element, and in response to actuation of the second user input element, the driving unit is configured to move the movable platform in a direction that is opposite to a direction in which the driving unit is configured to move the movable platform in response to actuation of the one or more user input elements.

In some applications, the container holder further includes a switch, which is configured to disable functioning of the driving unit during a first time period, and which is configured to not disable functioning of the driving unit during a second time period, and the switch is operable independently of the one or more user input elements. In some applications, the upper portion of the container holder includes a switch, which is configured to disable functioning of the driving unit when a cap of the container is disposed on the container, and the switch is configured to not disable functioning of the driving unit when the cap of the container is not disposed on the container. In some applications, the switch is disposed on an uppermost surface of the upper portion of the container holder.

In some applications, the lower portion includes a threaded shaft fixedly coupled to the driving unit, the threaded shaft being insertable into the movable platform of the container. In some applications, the threaded shaft is insertable into the movable platform without rotation of the threaded shaft with respect to the movable platform. In some applications, the threaded shaft is removable from the movable platform by rotation, and removal of the threaded shaft from the movable platform is inhibited in the absence of rotation of the threaded shaft with respect to the movable platform. In some applications, the threaded shaft is gradually removable from the movable platform by rotation of the threaded shaft that is induced by the driving unit during regular use of the apparatus. In some applications, the apparatus includes the container for dispensing the composition, and the threaded shaft is sized such that the threaded shaft is removed from the movable platform essentially upon completion of the composition in the container.

In some applications, the power source includes an electrical power source.

In some applications, the one or more user input elements include a detector, configured to detect proximity between an upper surface of the container and skin of a subject. In some applications, the container holder further includes a detector, configured to detect a parameter selected from the group consisting of: (a) proximity between an upper surface of the container and skin of a subject, and (b) contact between an upper surface of the container and skin of a subject, and the power source is operative to facilitate driving of the driving unit in response to the detection by the detector. In some applications, the power source is operative to inhibit driving of the driving unit in the absence of a detection of proximity by the detector, even in response to the actuation of the one or more user input elements. In some applications, the detector is coupled to an upper surface of the container holder. In some applications, the detector includes an optical proximity detector. In some applications, the detector includes a mechanical detector. In some applications, the mechanical detector includes at least one mechanical detector selected from the group consisting of: a pressure sensor and a mechanical switch. In some applications, the mechanical detector is configured to detect the proximity between the upper surface of the container and the skin of the subject by detecting a force between the container and the container holder. In some applications, the detector is configured to detect movement of the container with respect to the skin, while the detector is in contact with the skin. In some applications, the detector includes a roller.

In some applications, the container holder includes a digital display. In some applications, the digital display is operative to indicate at least one parameter selected from the group consisting of: a remaining amount of the composition, a time the apparatus has last been used, remaining life of a battery coupled to the apparatus, current time, current date, and a remaining number of applications of the composition.

In some applications, the container holder is fixedly coupled to the container.

In some applications, the apparatus is for use with a container, and the apparatus includes a light source. In some applications, the light source is configured to illuminate the composition in the container. In some applications, the light source is configured to be activated when a cap of the container is removed. In some applications, the light source is configured to be activated upon activation of one or more user input elements.

In some applications, the apparatus further includes a level indication element, which is arranged to indicate a remaining amount of the composition. In some applications, the level indication element is shaped to define a transparent slot in the container. In some applications, the level indication element is shaped to define a transparent slot in the container holder. In some applications, the level indication element is selected from the group consisting of: an electrically-conductive element, a magnetic element and an optically-reflective element. In some applications, the level indication element is configured to indicate a continuously-variable remaining amount of the composition. In some applications, the level indication element includes an indication light source, configured to indicate the remaining amount of the composition. In some applications, the indication light source is configured to indicate the remaining amount of the composition by flashing. In some applications, the indication light source is configured to indicate the remaining amount of the composition by changing color. In some applications, the apparatus further includes a vibration element, configured to be activated upon coupling of the container and the container holder. In some applications, the apparatus further includes a vibration element, configured to be activated upon actuation of the one or more user input elements. In some applications, the apparatus further includes a vibration element, configured to be activated when a cap of the container is removed.

There is further provided, in accordance with some applications of the present invention, apparatus including: a composition including at least one composition selected from the group consisting of: a deodorant and an antiperspirant; a container that contains the composition, the container including a movable platform configured such that movement of the platform dispenses the composition from the container, the apparatus being packaged for sale to a consumer and not including a shaft which by rotation thereof moves the platform up within the container.

In some applications, the composition includes a viscous composition, and the container includes an upper surface shaped to define a plurality of holes suitable for dispensing the viscous composition therethrough. In some applications, the composition is shaped as a solid stick composition, and the container is shaped to have an open upper surface suitable for facilitating passage therethrough of the solid stick composition. In some applications, the container and the container holder are fixedly coupled to one another. In some applications, the apparatus further includes a second user input element, and in response to actuation of the second user input element, the one or more user input elements are configured to activate the driving unit to move the movable platform in a direction that is opposite to a direction in which the driving unit is configured to move the movable platform in response to actuation of the one or more user input elements.

In some applications, the container includes a lower portion that is shaped to define an opening for passage of a shaft therethrough. In some applications, a cross-sectional area of the opening is 0.06 to 1 cm2. In some applications, a cross-sectional area of the opening is 1 to 25 cm2.

In some applications, the apparatus further includes a shaft threadedly engaged to the platform in a manner such that rotation of the shaft moves the shaft within the container while not moving the platform up within the container. In some applications, the apparatus is characterized in that downward motion of the shaft within the container is not restricted during rotation of the shaft, but if downward motion of the shaft within the container were to be restricted during rotation of the shaft, then rotation of the shaft in one direction would move the platform up within the container. In some applications, the movable platform is not threadedly coupled to a shaft. In some applications, the movable platform is shaped to define a threaded hole. In some applications, the movable platform is not threadedly coupled to a shaft, the movable platform is shaped to define a hole, the apparatus is for use with a threaded shaft, and the movable platform includes flexible threaded segments which surround the hole and which facilitate insertion of the threaded shaft through the hole, without rotation of the shaft, by bending away from an axis of the shaft upon insertion of the shaft through the threaded hole. In some applications, following insertion of the shaft through the threaded hole, the flexible threaded segments are configured to threadedly engage the threaded shaft.

In some applications, the apparatus is for use with a container holder, and a lower surface of the container is shaped to define at least one surface selected from the group consisting of: a round surface, a convex surface, a grooved surface, a wavy surface, and a toothed surface, to correspond to a corresponding surface of the container holder.

In some applications, the apparatus is for use with a container holder, and the container includes a user-activatable release mechanism operative to release the container from the container holder. In some applications, the user-activatable release mechanism includes an energy-storage element, which is configured to store energy by deformation thereof, upon initial coupling of the container to the container holder, and which is configured to release the stored energy during the coupling of the container to the container holder, prior to actuation of the user-activatable release mechanism. In some applications, the container is operative to become locked to the container holder by means of the release of the stored energy during the coupling of the container to the container holder, prior to actuation of the user-activatable release mechanism.

In some applications, the container includes a detectable element disposed between 2 and 5 cm of a bottom-most surface of the container, the detectable element being selected from the group consisting of: an electrically-conductive element, a magnetic element, and an optically-reflective element. In some applications, the container includes a detectable element disposed between 2 and 5 cm of a upper-most surface of the container, the detectable element being selected from the group consisting of: an electrically-conductive element, a magnetic element, and an optically-reflective element. In some applications, the container includes an electrically-conductive element at least 1 cm in length disposed on an outer surface of the container. In some applications, the electrically-conductive element is at least 5 cm in length and is not straight. In some applications, the apparatus is for use with a container holder that includes an electronic circuit, and the electrically-conductive element is positioned such that upon coupling of the container to the container holder, the electrically-conductive element closes the electronic circuit.

In some applications, the apparatus further includes a cap removably placeable on the container, the cap having a lower surface that is shaped to define at least one shape characteristic selected from the group consisting of: at least one indent and at least one protrusion. In some applications, the at least one shape characteristic is selected from the group consisting of: at least two indents and at least two protrusions. In some applications, the apparatus is for use with a container holder having a switch, and the at least one shape characteristic of the cap is configured to activate the switch upon coupling of the cap to the container when the container holder is also coupled to the container.

In some applications, the apparatus as packaged for sale to the consumer includes a battery that is disposable within the container, the battery not being configured to supply electricity to any component of the apparatus that (a) is included in the apparatus as packaged for sale to the consumer and (b) may drive the movable platform.

In some applications, the apparatus is for use with a container holder, and a portion of the container is shaped to define a predefined surface shape configured to couple to a corresponding predefined surface shape of the container holder, and configured to inhibit slipping of the container from the container holder.

There is further provided, in accordance with some applications of the present invention, apparatus for use with a container that contains a composition, the container including a movable platform, the apparatus including: a container holder including: an upper portion, which includes one or more user input elements; and a lower portion including a driving unit and a power source, the power source is operative to drive the driving unit to move the movable platform of the container, in response to actuation of the one or more user input elements.

In some applications, the composition is selected from the group consisting of: a deodorant, an antiperspirant, a skin-care composition, a composition including a pharmaceutical composition, a cosmetic composition, and an ultrasound gel composition, and the apparatus is for use with the container containing the selected composition. In some applications, the selected composition includes the cosmetic composition, and the apparatus is for use with the container containing the cosmetic composition. In some applications, the selected composition includes the skin-care composition, and the apparatus is for use with the container containing the skin-care composition. In some applications, the skin-care composition includes face cream, and the apparatus is for use with the container containing the face cream. In some applications, the selected composition includes the pharmaceutical composition, and the apparatus is for use with the container containing the pharmaceutical composition. In some applications, the pharmaceutical composition includes a hormone, and the apparatus is for use with the container containing the pharmaceutical composition including the hormone. In some applications, the hormone includes a steroid hormone, and the apparatus is for use with the container containing the pharmaceutical composition including the steroid hormone. In some applications, the hormone includes testosterone, and the apparatus is for use with the container containing the pharmaceutical composition including the testosterone. In some applications, the hormone includes cortisone, and the apparatus is for use with the container containing the pharmaceutical composition including the cortisone.

There is further provided, in accordance with some applications of the present invention, apparatus including: a composition; a container that contains the composition, the container including a movable platform configured such that movement of the platform dispenses the composition from the container, the apparatus being packaged for sale to a consumer and not including a shaft which by rotation thereof moves the platform up within the container.

BRIEF DESCRIPTION OF THE DRAWINGS

The present invention will be fully understood from the detailed description and the accompanying drawings, wherein:

FIG. 9A shows an embodiment with an exemplary user-activatable release mechanism.

FIG. 9B shows a sectional view of the user-activatable release mechanism shown in FIG. 9A.

FIG. 9C shows an enlarged view of the user-activatable release mechanism shown in FIG. 9B.

FIG. 15 shows another platform that allows insertion of the shaft in one direction without the need for rotation.

FIG. 16A shows an embodiment of a container holder where the shaft is fixedly coupled to the driving unit.

FIG. 16B shows an embodiment of a container comprising the platform of FIG. 15.

DETAILED DESCRIPTION OF THE INVENTION

The following description of some embodiments is exemplary and should not limit the invention.

Figure 1:
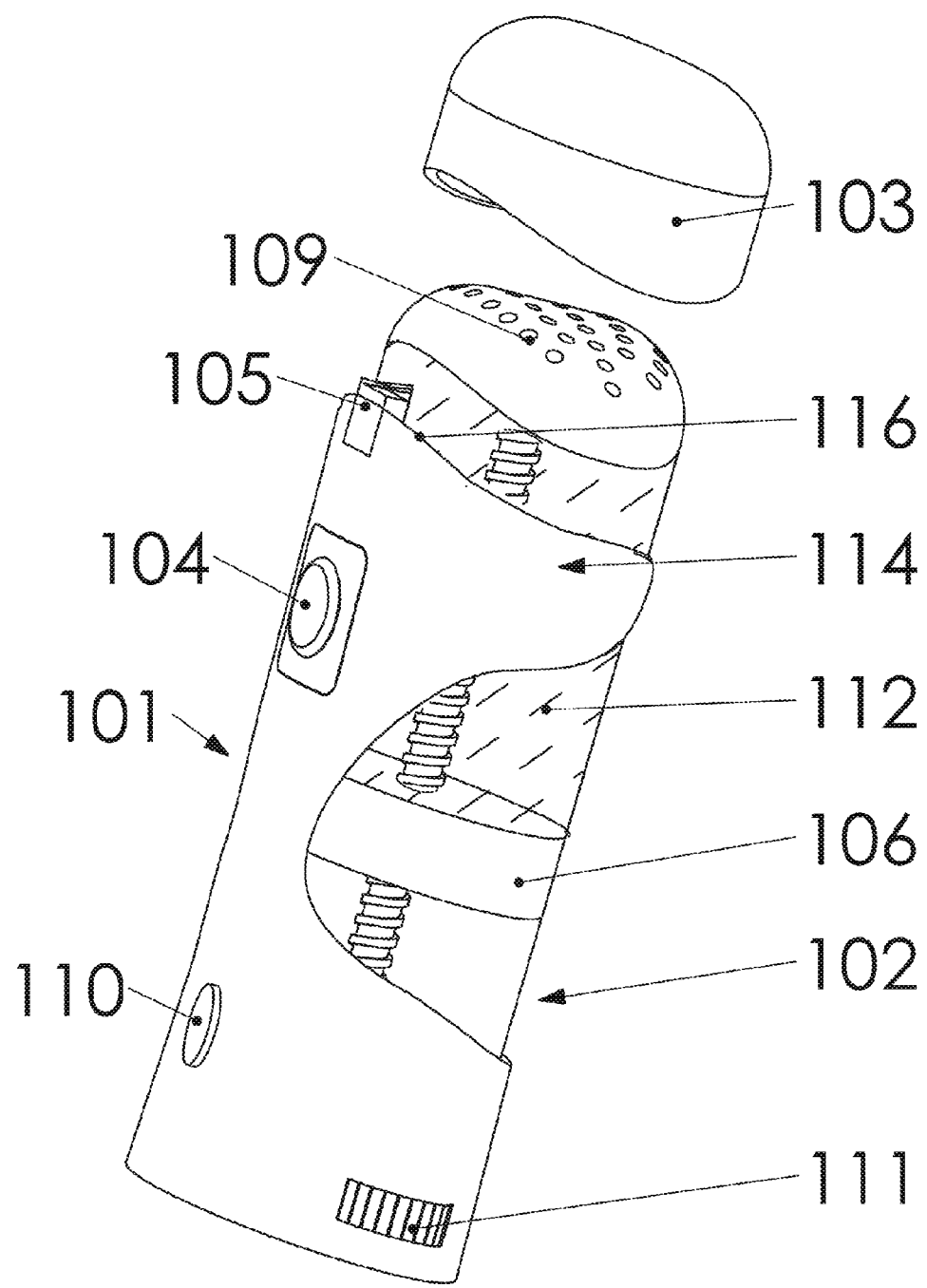
FIG. 1 shows a perspective side view of an embodiment of the apparatus for dispensing deodorant or antiperspirant.

FIG. 1 schematically illustrates a perspective view of an apparatus for dispensing a viscous fluid composition such as deodorant/antiperspirant. The composition may alternatively comprise a skin-care composition, a composition including a pharmaceutical composition, a cosmetic composition, or an ultrasound gel composition. The apparatus comprises a container holder 101 coupled to a container 102 that comprises the composition 112. The container holder 101 and the container 102 may be two separate entities (i.e., attachable and detachable by the user) or in some embodiments may be one entity. In some embodiments, the container 102 can be refilled with a composition or replaced by a new container. In this case, the user may keep the container holder 101 while replacing the container 102 after the composition 112 has been dispensed. In these embodiments, the release of the container 102 from the container holder 101 is done by pressing the user-activatable release mechanism button 110, operative to release the container from the container holder. The container 102 may or may not be transparent (the container shown in this figure is transparent). The container holder 101 contains one or more user input elements 104 for dispensing the composition. When the user input element 104 is actuated, the composition is dispensed. The user input element 104 may comprise an electronic user input element, or a non-electronic user input element (e.g., a mechanical user input element). The user input element 104 may be a push button. According to tests that were done by the inventors, it was found that for convenience of use, the user input element should be located around mid-height of the apparatus. More specifically, it was found that the user input element 104 should typically be disposed on an upper 75% of the container holder 101, e.g., on an upper 50% or 40% of the container holder 101. For some applications, the one or more user input elements are configured to be placed in a vicinity of an upper 75% of the container, when the container is coupled to the container holder, e.g., in a vicinity of an upper 50% of the container. The container holder 101 may also comprise an upper portion 114 configured to couple the upper portion of the container holder to the container.

Figure 2:
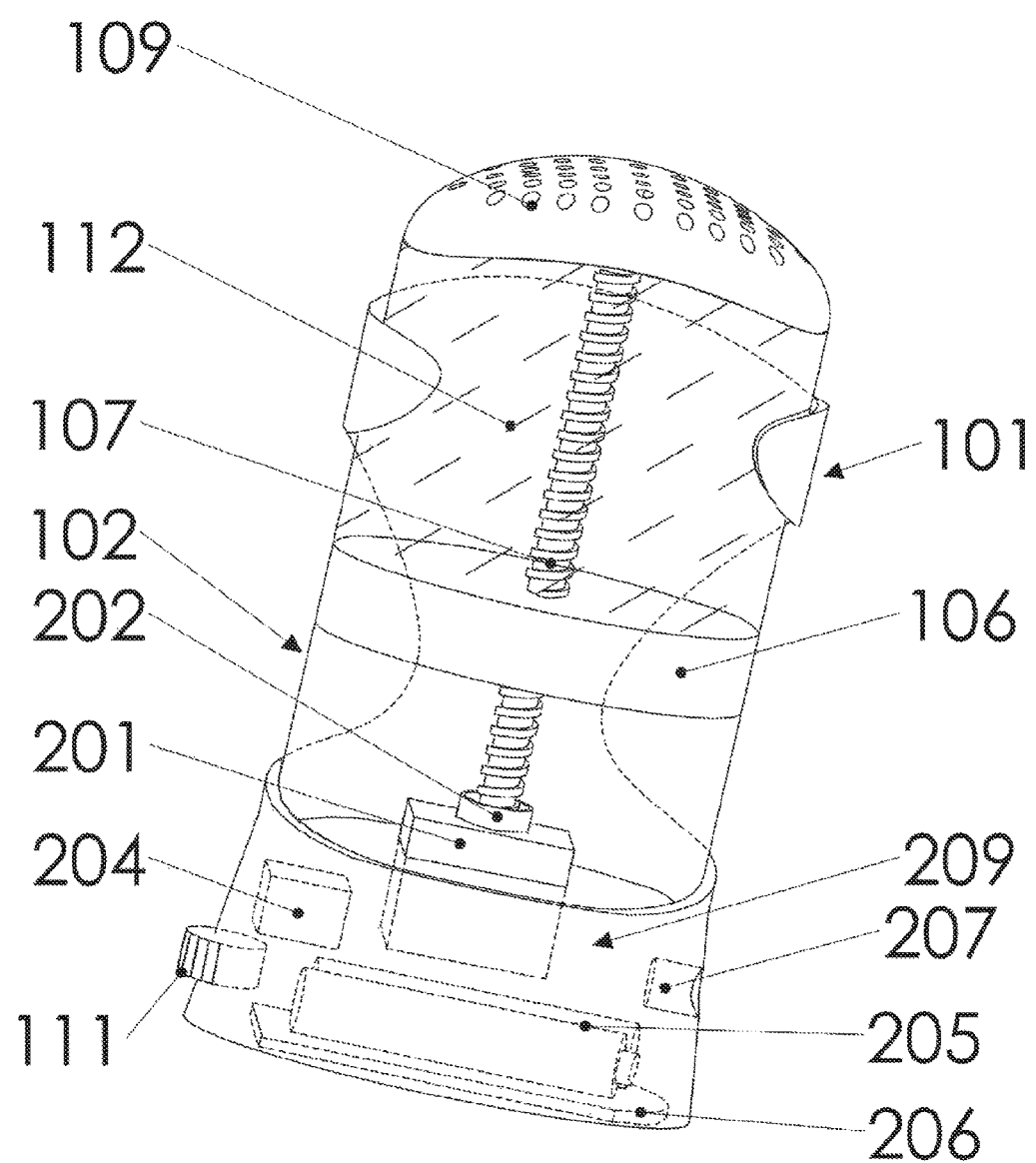
FIG. 2 shows a perspective front view of the embodiment shown in FIG. 1 with inner parts of the container holder shown in phantom.

The container holder 101 may further comprise a user input element (e.g. switch) 105, which is configured to disable functioning of the driving unit 201 shown in FIG. 2 during a first time period, and which is configured to not disable functioning of the driving unit 201 during a second time period, wherein the user input element 105 is operable independently of the one or more user input elements. The first time period is defined as the time when the apparatus is not intended to be used. The second time period is defined as the time when the apparatus is intended to be used. This user input element 105 can be located anywhere on the container holder, and not just as shown in FIG. 1. In the embodiment presented in FIG. 1, the user input element 105 comprises a switch, located on the upper portion of the container holder 114. The container 102 may be closed by the cap 103. The switch 105 may be configured to disable functioning of the driving unit 201 when a cap of the container is disposed on the container, and to not disable functioning of the driving unit 201 when the cap of the container is not disposed on the container. The switch 105 may be disposed on an uppermost surface 116 of the upper portion 114 of the container holder 101. The driving unit 201 is typically powered by a power source. If the power source comprises batteries, the switch 105 serves to extend the batteries' life. In addition, the switch 105 prevents operation of the apparatus by accidental actuation of the user input element 104 when the cap 103 is closed.

In some embodiments, the driving unit 201 may be configured to move the movable platform 106 a predetermined distance in response to actuation of the one or more user input elements. In this case, the container holder 101 may include a portion-quantity input element 111, configured to receive an indication of a desired quantity of the composition, and the apparatus is operative to set the predetermined distance based on the indication of the desired quantity. The portion quantity input element 111 may be a turning knob, as shown in FIG. 1, which gives the user full control over the range, or a knob which allows one of a plurality of preset amounts. The knob 111 can be located on any external surface of the apparatus. In another embodiment, the knob 111 may be omitted and the amount may be preset by the manufacturer. In this case, the predetermined distance is a fixed distance and the driving unit 201 is configured to move the movable platform the fixed distance, in response to actuation of the one or more user input elements. Alternatively, the amount is not controlled, and the user sets the amount based on the duration of actuating the user input element 104. The container may comprise an upper surface shaped to define a plurality of holes 109 suitable for dispensing the viscous composition 112. These holes may be of any shape, size and number as appropriate, and arranged in different patterns according to the desired composition.

FIG. 2 illustrates a perspective front view of the apparatus for dispensing a composition selected from the group consisting of: a deodorant, an antiperspirant, a skin-care composition, a composition including a pharmaceutical composition, a cosmetic composition, and an ultrasound gel composition, the container 102 including a movable platform 106. The container holder 101 comprises a lower portion 209 comprising a driving unit 201 and a power source 205, and the power source 205 is operative to drive the driving unit 201 to move the movable platform 106 of the container 102, in response to actuation of the one or more user input elements (104 and 105 (FIG. 1), for example). Some components located in the lower portion 209 of the container holder 101 are shown in phantom for illustration purposes. In the case of a viscous fluid, the composition 112 is confined between the platform 106 and the plurality of holes 109, inside the container 102. The platform lifting mechanism typically includes a driving unit 201 coupled to a threaded shaft 107 through a coupling mechanism 202. The shaft 107 threadedly engages a platform 106 through a threaded hole. The thread of the shaft can be of any pitch and can either be a right-handed or left-handed thread. Rotary motion of the driving unit 201 causes the platform 106 to advance upwardly on the threaded shaft 107. This upward motion of the platform 106 forces the composition 112 upwardly through the plurality of holes 109. In an embodiment where the container 102 is detachable from the container holder 101, the coupling mechanism 202 is necessary. In this case, the lower end of the shaft 107 has a shape that couples to the coupling mechanism 202 in the container holder 101. In another embodiment, where the container 102 or the shaft 107 is fixedly coupled to the container holder 101, the coupling mechanism 202 may not be used, and the driving unit 201 may be directly connected to the shaft 107. Optionally, if the container holder 101 is detachable from the container 102, the latter may contain the platform 106 and the shaft 107 or a platform without a shaft. In this figure, some of the components that may be included in the lower portion 209 of the container holder 101 are shown in phantom. As can be seen, the container holder 101 may include in addition to the driving unit 201, an electronic circuit 204 and a power source 205 that may comprise an electrical power source. In this exemplary embodiment, the power source 205 comprises batteries with a battery cover 206. Optionally, the electronic circuit 204 and the driving unit 201 may be powered/charged by an external power source through the power inlet 207. The electronic circuit 204 may be powered by the power source 205, and its electronic components may vary according to the desired operation and may comprise a controller, reverse drive and a time controller or any other components, which are apparent to those skilled in the art having read the specification of the present patent application. The controller may operate the driving unit 201 to move the movable platform a predetermined distance in response to actuation of the one or more user input elements. The predetermined amount of composition may be set by the user using a user input element such as a switch/knob 111, or alternatively may be preset by the manufacturer. In either case, the electronic circuit 204 produces repeatability of the amount dispensed each time the apparatus is used. Alternatively, in another embodiment, the electronic circuit may not include components to preset the amount to be dispensed. In this case, the user presses on the user input element 104 and controls the amount dispensed by releasing the user input element 104 after a desired amount of composition has been dispensed. Note that in this figure, a part of the driving unit 201 and the coupling mechanism 202 can be seen outside of the base but in other embodiments, the driving unit 201 and the coupling mechanism 202 may be completely hidden inside the container holder 101.

Figure 3:
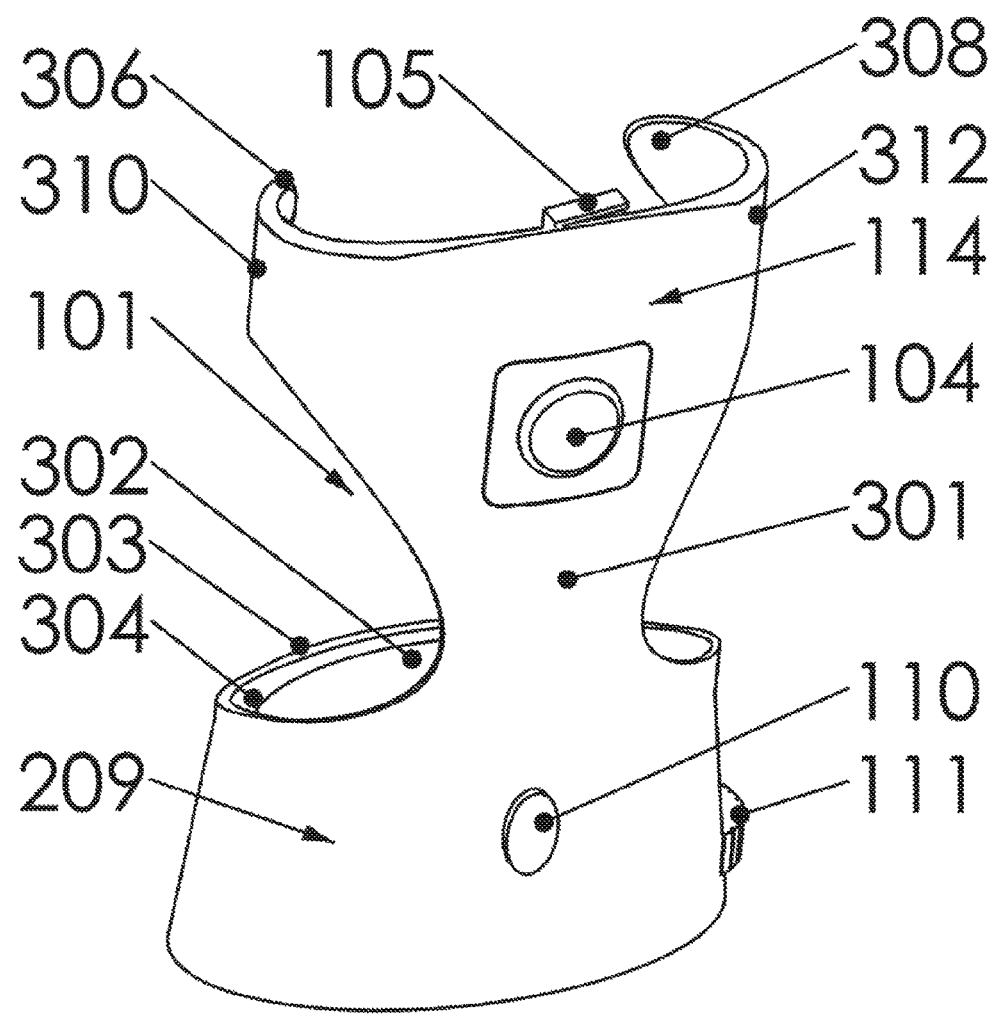
FIG. 3 shows a perspective back view of the container holder of FIG. 1.

As shown in FIG. 1 and FIG. 2, the apparatus is for use with a container 102 for dispensing a composition including at least one composition selected from the group consisting of: a deodorant, an antiperspirant, a skin-care composition, a pharmaceutical composition, a cosmetic composition, and an ultrasound gel composition. The container typically includes a movable platform 106 while the apparatus comprises a container holder 101 as shown in FIG. 3. The container holder comprises an upper portion 114, which comprises one or more user input elements (e.g. 104 and 105); and a lower portion 209 comprising a driving unit 201 and a power source 205 (shown in FIG. 2), wherein the power source is operative to drive the driving unit to move the movable platform 106 of the container 102, in response to actuation of the one or more user input elements.

FIG. 3 is a perspective back view of the container holder 101 without the container 102. The container holder 101 typically serves one or more of several functions in the operation of the apparatus. As shown in FIG. 2, the container holder 101 contains the driving unit, the power source and the electronics used for the operation. An element in operating the apparatus is pressing the user input element 104 to dispense the composition. Therefore, the input element 104 should be located in a convenient location allowing the user easy operation while holding the apparatus in one hand. Trials performed by the inventors showed that a suitable location for the input element 104 is on the upper 75% of the apparatus. To serve this purpose, the upper portion 114 of the container holder 101 is shaped in part to define a spine 301, extending up from the lower portion 209 of the container holder 101. This extension of the container holder upwardly also allows the container holder 101 to include the user input element 105 comprising a switch that is pressed when the cap 103 (shown in FIG. 1) is in place. In the shown embodiment, the container holder upper portion 114 is shaped to define a container-coupling upper portion, configured to couple the upper portion of the container holder to the container. In this embodiment, container-coupling upper portion 114 comprises one or more grips 306 and 308, which are configured to hold an upper portion of the container. The grips 306, 308 extending from the spine 301 are configured to prevent the spine from bending by holding the spine 301 in contact with the container 102. Holding the spine in contact with the container provides that the switch 105 will be in contact with the cap 103. By using a less flexible material, the grips 306 and 308 may not be used (e.g., as shown FIG. 17). In this embodiment, the grips 306 and 308 comprise exactly two wings 310 and 312 configured to simultaneously apply a pressing force to the container. The lower portion 209 also comprises a cavity 304 located between the outer surface 303 and the inner surface 302. The cavity 304 is where the container 102 sits when coupled to the container holder 101.

Figure 4A:
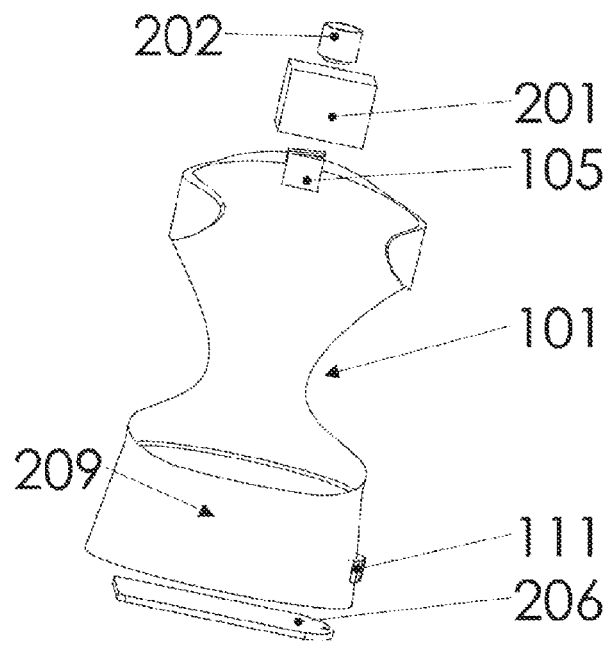
FIG. 4A illustrates an exploded view of an embodiment of the container holder.
Figure 4B:
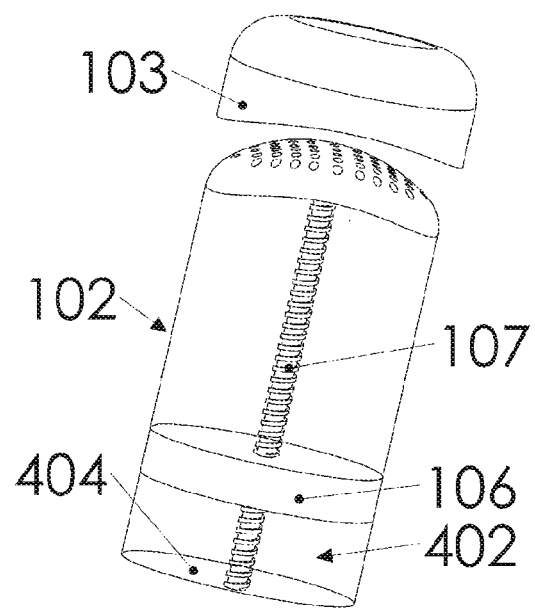
FIG. 4B shows an exemplary container comprising a platform and a shaft and closed by a cap. In this embodiment, the container may fit to the container holder of FIG. 4A.

FIG. 4A presents an exploded view of the container holder 101, while FIG. 4B shows the container 102. In these figures, the container holder 101 is decoupled from the container 102. In FIG. 4A, the coupling mechanism 202 and the driving unit 201 of FIG. 2 are seen outside the lower portion 209 of the container holder 101. In this embodiment where the power source may comprise replaceable batteries, a battery cover 206 can be seen. In another embodiment where the power source may not comprise replaceable batteries, the battery cover 206 may be omitted.

In FIG. 4B, the container 102 comprises the shaft 107 and the platform 106. When decoupled from the container holder 101, the container 102 does not comprise a shaft which by rotation moves the platform 106 up within the container. The shaft 107 is threadedly engaged to the platform in a manner such that rotation of the shaft moves the shaft within the container while not moving the platform 106 up within the container. This results from the fact that the container 102 comprises a lower portion 402 that is shaped to define an opening 404 for passage of the shaft 107. Therefore, downward motion of the shaft 107 within the container 102 is not restricted during rotation of the shaft 107, but if downward motion of the shaft 107 within the container 102 were to be restricted during rotation of the shaft 107 (e.g., when the container is coupled to the container holder), then rotation of the shaft 107 in one direction would move the platform 106 up within the container 102. In FIG. 4B, the container is open at the lower portion and therefore the opening 404 comprises the whole cross-sectional area of the lower surface of the container 102. In some embodiments, the cross-sectional area of the opening 404 may vary from 25 cm2 to 0.06 cm2 (cross-sectional area of a relatively small shaft). Note that conventional deodorant dispensers comprise a turn-buckle to facilitate rotation of the shaft 107 in order to lift the platform 106. As can be seen in this figure, applications of this invention are different since there is no turn-buckle and lifting the platform is done by coupling the container 102 to the container holder 101 and operating the driving unit. Once the container 102 is coupled to the container holder 101 (e.g., by the user), the container holder 101 is typically an integral part of the apparatus and it is not a separate entity during use. Typically, the size of the apparatus when the container is coupled to the container holder is similar to the size of conventional deodorant dispensers. In addition, more specifically, the size of the lower portion 209 of the container holder 101 is typically small relative to the size of the container 102. This feature is illustrated in FIG. 4A.

Figure 5:
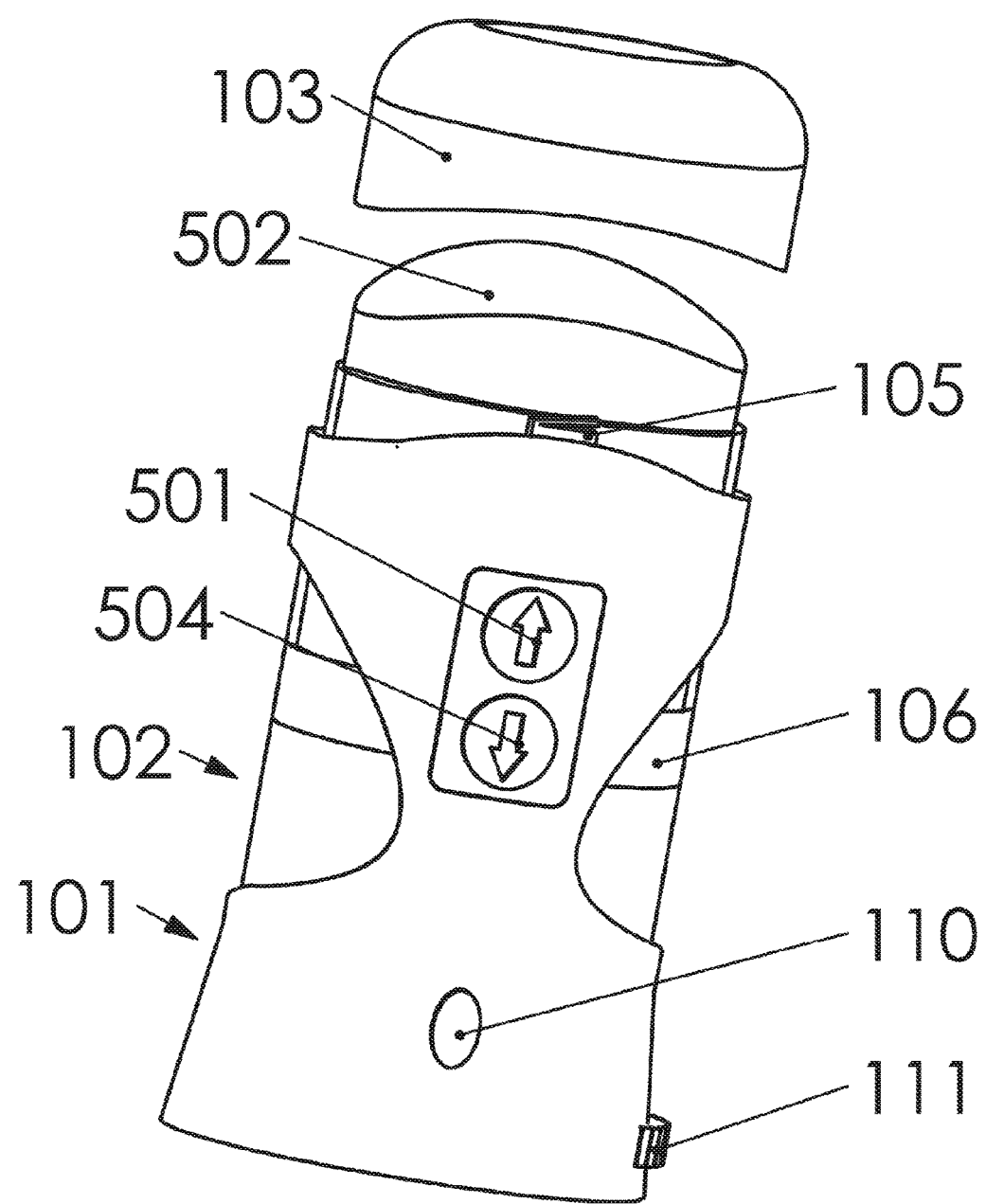
FIG. 5 shows an embodiment for use with a solid stick composition.

In some exemplary embodiments, as shown in FIG. 5, the composition is shaped and provided as a solid stick 502. In this case, the container is shaped to have an open upper surface suitable for facilitating passage of the solid stick composition. In this embodiment, the user input element 104 (shown in FIG. 1) may be replaced by a user input element, further comprising two user input elements 501 and 504. In response to actuation of the second user input element 504, the driving unit 201 is configured to move the platform 106 in a direction that is opposite to the direction in which the driving unit 201 is configured to move the platform 106 in response to actuation of the first user input element 501. The reverse drive mechanism is used when the apparatus comprises a solid stick composition, in which case the reverse drive mechanism is used to retract the composition back by moving the platform 106 down.

In another embodiment, e.g., one in which the composition is a viscous gel, the reverse drive mechanism may be included in the electronic circuit 204 (shown in FIG. 2) to prevent leakage of the viscous gel. In addition, the reverse drive mechanism can be used to facilitate refilling of an empty container 102. The reverse drive feature may be controlled automatically by the electronic circuit or using an additional user input element that can be located anywhere on the apparatus. The user input elements 501 and 504 in FIG. 5 are an example. Alternatively, the reverse drive mechanism can be controlled or partially controlled by closing the cap 103, whereby the composition automatically retracts when the cap 103 is closed.

The driving unit 201 (shown in FIG. 2) typically comprises an electric motor that may be a direct drive motor, a geared motor or a motor connected to a separate gearbox. The driving unit 201 may include electronics, which allow angular position monitoring or control (for example a stepper motor, a servo motor, or a DC motor with an encoder). The operation of the driving unit 201 causes the threaded shaft 107 to rotate. The driving unit 201 may be connected to the threaded shaft 107 through a coupling mechanism 202 to be discussed in FIG. 6A, FIG. 6B, and FIG. 7.

Figure 6A:
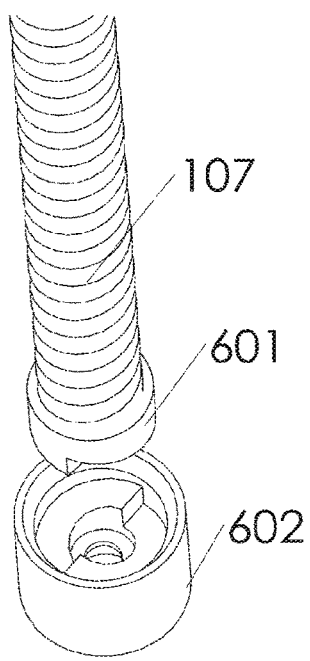
FIG. 6A illustrates an example of a coupling mechanism that connects the shaft to the driving unit.
Figure 6B:
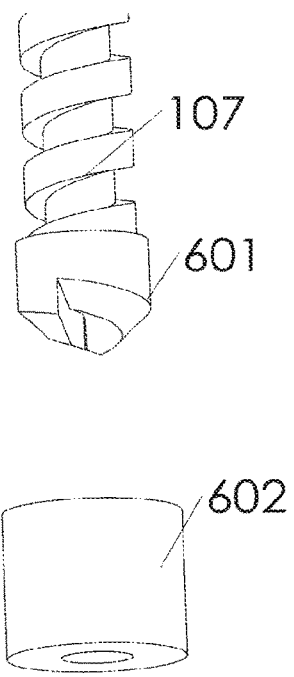
FIG. 6B illustrates a different view of the coupling mechanism shown in FIG. 6A.

An example of the coupling mechanism 202 (shown in FIG. 2) is illustrated in FIG. 6A and FIG. 6B. The coupling mechanism connects the shaft 107 to the driving unit 201 and comprises two helically shaped parts 601 and 602. The first part 601 is located at the bottom end of the shaft 107 and connects to helically shaped part 602, which is located at the top end of the driving unit 201. Parts 601 and 602 have a complementary helically shaped construction that provides the desired engagement and prevents slipping of the shaft 107 with respect to helically shaped part 602 when the shaft 107 is rotated by helically shaped part 602. In another embodiment, parts 601 and 602 may be interchanged in such a way that part 601 is located at the top end of the driving unit 201 and part 602 is located at the bottom end of the shaft 107. In embodiments where the container is detachable from the container holder for refill purposes, the coupling mechanism as shown in FIG. 6A and FIG. 6B typically provides easy, precise and self-centering reattachment of the new container to the container holder. Alternatively, 601 may be an integral part of the shaft 107 and not a separate entity and hence, in this case, the bottom end of the shaft 107 is manufactured in a desired shape that complements the second part 602 located at the top of the driving unit 201. The coupling mechanism presented in FIG. 6A and FIG. 6B allows rotation in one direction and therefore the helical parts 601 and 602 can be manufactured to allow either clockwise rotation or counterclockwise rotation.

Figure 7:
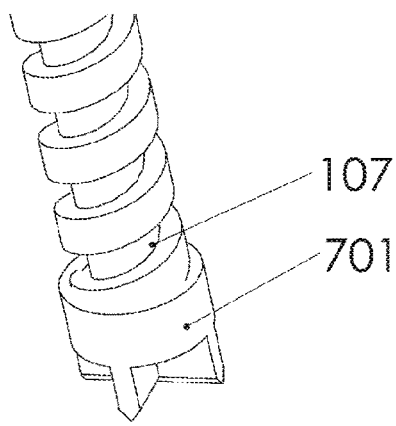
FIG. 7 illustrates another example of the coupling mechanism that connects the shaft to the driving unit.
Figure 7:
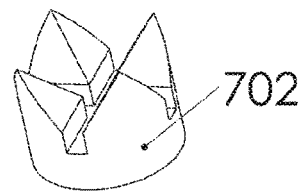

In another embodiment, another coupling mechanism may be implemented as shown in FIG. 7. The main difference between the coupling mechanisms presented in FIG. 6A (or FIG. 6B) and FIG. 7 is that the latter allows rotation in both directions.

As shown in FIG. 7, part 701 is located at the bottom end of the shaft 107 and connects to part 702, which is located at the top end of the driving unit 201. This is a no-slippage, bi-directional coupling. Parts 701 and 702 have a complementary tapered jaw shape construction that provides the desired engagement and prevents slipping of the shaft 107 with respect to part 702 when the shaft 107 is rotated by part 702. In embodiments where the container is detachable from the container holder for refill purposes, the coupling mechanism as shown in FIG. 7 typically provides easy, precise and self-centering reattachment of the new container to the container holder. Alternatively, 701 may be an integral part of the shaft 107 and not a separate entity and hence, in this case, the bottom end of the shaft 107 is manufactured in a desired shape that complements the second part 702 located at the top of the driving unit 201.

Figure 8A:
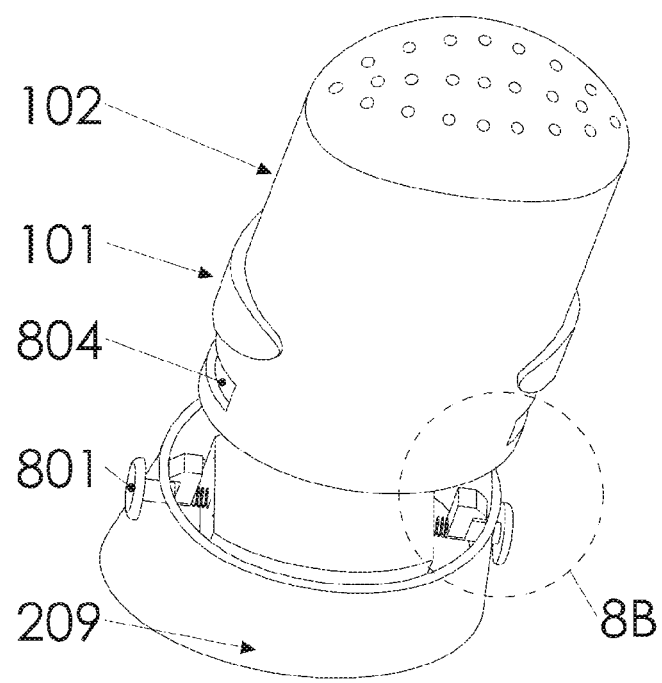
FIG. 8A shows an embodiment with an exemplary user-activatable release mechanism.
Figure 10:
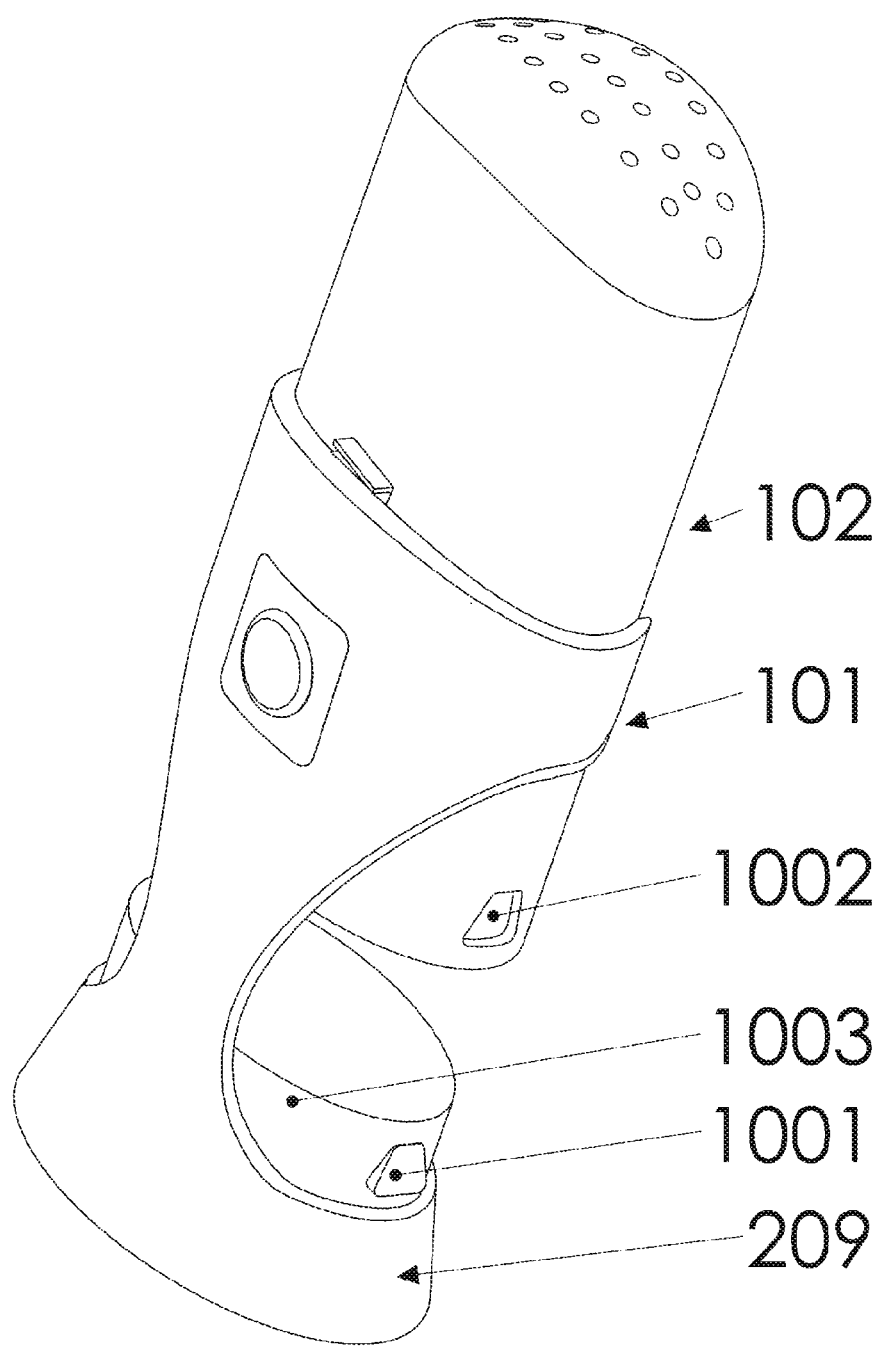
FIG. 10 shows another example of a user-activatable release mechanism.

As previously mentioned the container 102 may be detachable from the container holder 101 and replaced by another container for refill purposes. The container 102 or the container holder 101 may comprise a user-activatable release mechanism operative to release the container from the container holder. The user-activatable release mechanism may be disposed on the lower portion 209 or upper portion 114 (shown in FIG. 3) of the container holder 101. FIG. 8A, FIG. 9A and FIG. 10 show optional release mechanisms.

Figure 8B:
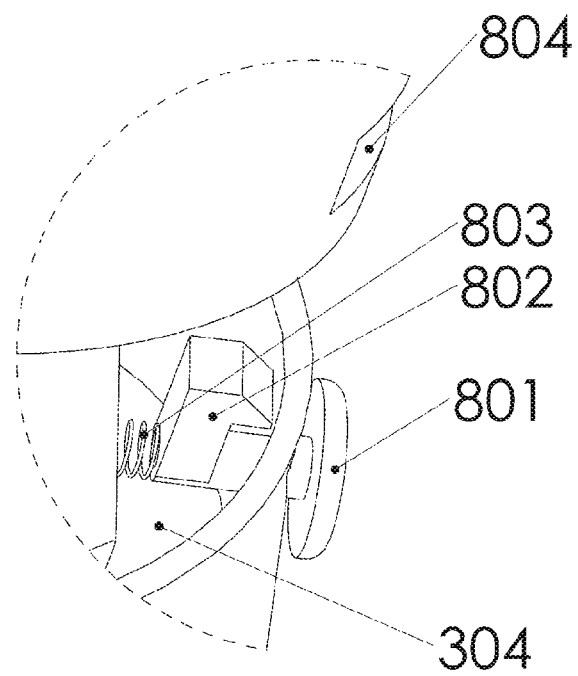
FIG. 8B shows an enlarged view of the user-activatable release mechanism shown in FIG. 8A.

FIG. 8A shows an exemplary release mechanism with an enlarged view shown in FIG. 8B. In these figures, two user-activatable buttons 801 are located on the lower portion 209 of the container holder 101. The locking tabs 802 are attached to the release buttons 801 from one side and pushed by an energy storage element 803 (e.g. spring), on the other side. Upon initial coupling of the container to the container holder, the energy-storage element 803 stores energy by deformation and is configured to release the stored energy during the coupling of the container to the container holder when the locking tabs 802 meet the cavities 804 and secure the apparatus in the cavity 304. When the user actuates the release buttons 801 and deforms the energy storage element 803, the locking tabs 802 disengage from the cavities 804 allowing disengagement of the container 102 from the container holder 101. This user-activatable release mechanism is known to those skilled in the art. In this embodiment, two user-activatable release buttons are shown. Alternatively, only one user-activatable release button 110 is used as can be seen in FIG. 1 and FIG. 3.

FIG. 9A shows an embodiment with another exemplary release mechanism with FIG. 9B showing a sectional view of the same embodiment and an enlarged view is shown in FIG. 9C. In the exemplary embodiment shown, when coupled to the container holder 101, the container 102 may sit within a cavity 903 located in the container holder 101. One or more user-activatable release buttons 901 may be located on the container 102. These user-activatable release buttons can be located anywhere on the container 102. Optionally, the container holder 101 and the container 102 are coupled through locking tabs 902 located on the container 102. Both the locking tabs 902 and the user-activatable release buttons 901 are connected through an energy storage element 905. In this embodiment, the energy storage element 905 relies on the flexibility of the container material. Upon initial coupling of the container to the container holder, the energy-storage element 905 stores energy by deformation and is configured to release the stored energy during the coupling of the container to the container holder when the locking tabs 902 meet the cavities 907, and secure the container in the cavity 903. When the user actuates the user-activatable release buttons 901 and deforms the energy storage element 905, the locking tabs 902 disengage from the cavities 907, allowing disengagement of the container 102 from the container holder 101. This user-activatable release mechanism is known to those skilled in the art. In this embodiment, two user-activatable release buttons are shown. Alternatively, only one user-activatable release button 110 may be used as can be seen in FIG. 1 and FIG. 3.

In another exemplary embodiment shown in FIG. 10, the container 102 may engage to the container holder 101 from the outside, surrounding a surface 1003. In this figure, the container 102 is not shown as transparent. In this embodiment, one or more user-activatable release buttons 1001 may be located on the container holder 101. These buttons can be located anywhere on the container holder 101 and may be spring-loaded or rely on the flexibility of the material as presented in FIG. 8A and FIG. 9B, respectively. The release buttons 1001 lock to mating grooves 1002 located on the container 102, as is known to those skilled in the art. In this exemplary embodiment, the release buttons 1001 are located in the lower portion 209 of the container holder 101. This is only an example and in other embodiments, the release mechanism may be located in any convenient place on the apparatus.

In another embodiment (similar to the embodiment shown in FIG. 1), the container 102 is tightly fitted to the container holder 101 and the release is done by manually forcing the container 102 out of the container holder 101. In this case, the user-activatable release button 110 is omitted. Optionally, the container 102 may be detached from the container holder 101 by the driving unit 201. As the platform 106 reaches the uppermost surface 116 of the container 102, further activation of the lifting mechanism pushes the platform 106 against the uppermost surface 116, which results in the container 102 being released from the container holder 101.

All the exemplary release mechanisms presented above may be spring-loaded to facilitate detachment and assembly. Also, these release mechanisms may utilize the flexibility of the material used to implement the container holder 101, the container 102 and the different components of the release mechanism. The material may be chosen according to the flexibility or rigidity suitable for the release mechanism to be easily operated and durable. In some exemplary embodiments, the apparatus is equipped with a way to let the user know when the container 102 is correctly engaged to the container holder 101. This may be a clear clicking sound from the mechanical engagement, a vibration or an audible signal.

Figure 11:
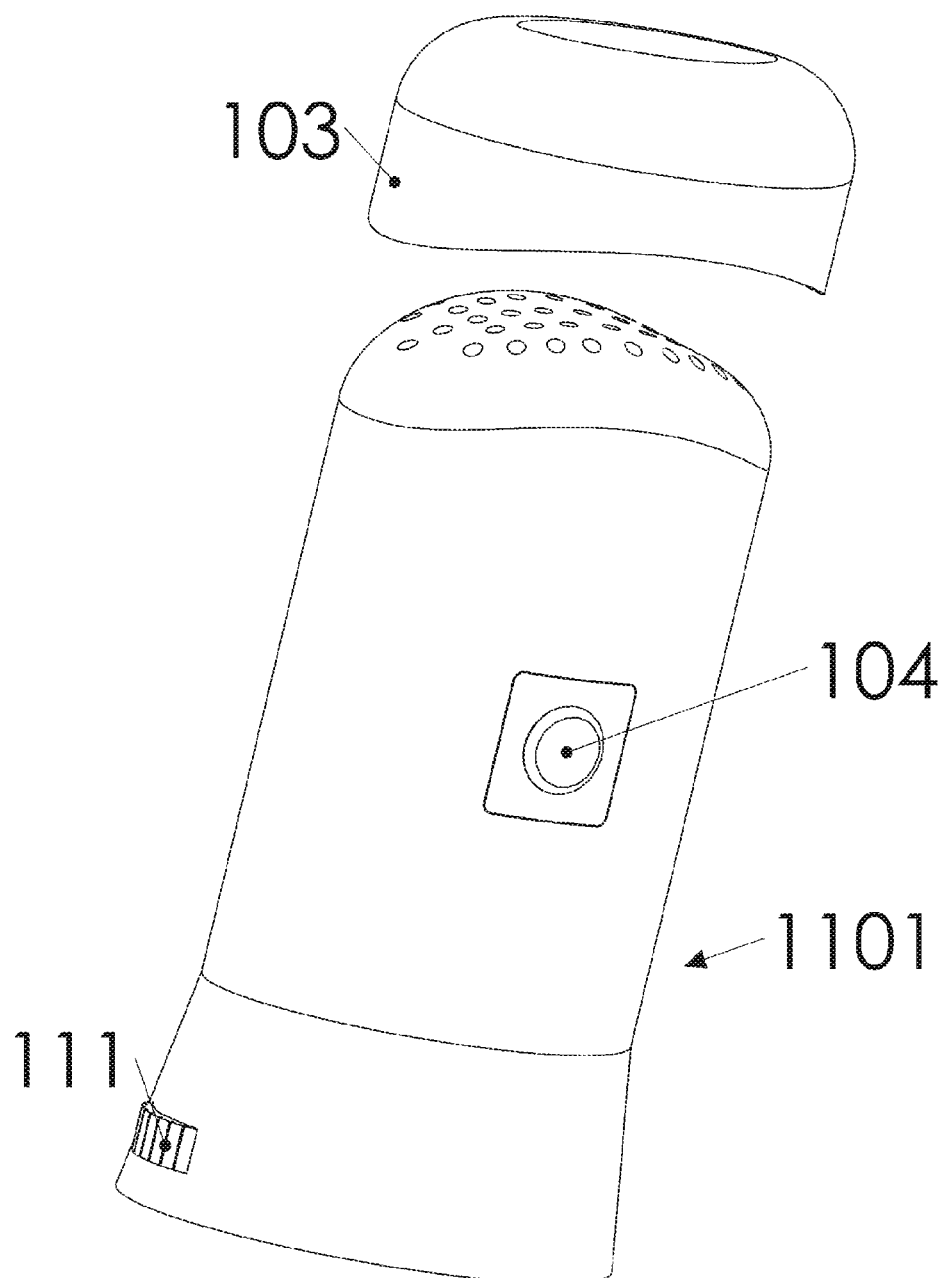
FIG. 11 illustrates another embodiment where the container and the container holder form one entity.

In another embodiment, shown in FIG. 11, the apparatus may comprise one inseparable unit 1101 where the container holder is fixedly coupled to the container. This embodiment contains all the features described above; however the container holding the composition is not detachable from the driving unit and they form one inseparable system 1101. The driving unit 201 and the electronic circuit 204 may be located in any convenient place inside the apparatus 1101. Also, the user input element 104 may be located anywhere on the outer surface of the apparatus 1101. In this embodiment, the consumer may refill the apparatus when the composition is all dispensed or alternatively may replace it with a new apparatus.

Figure 12:
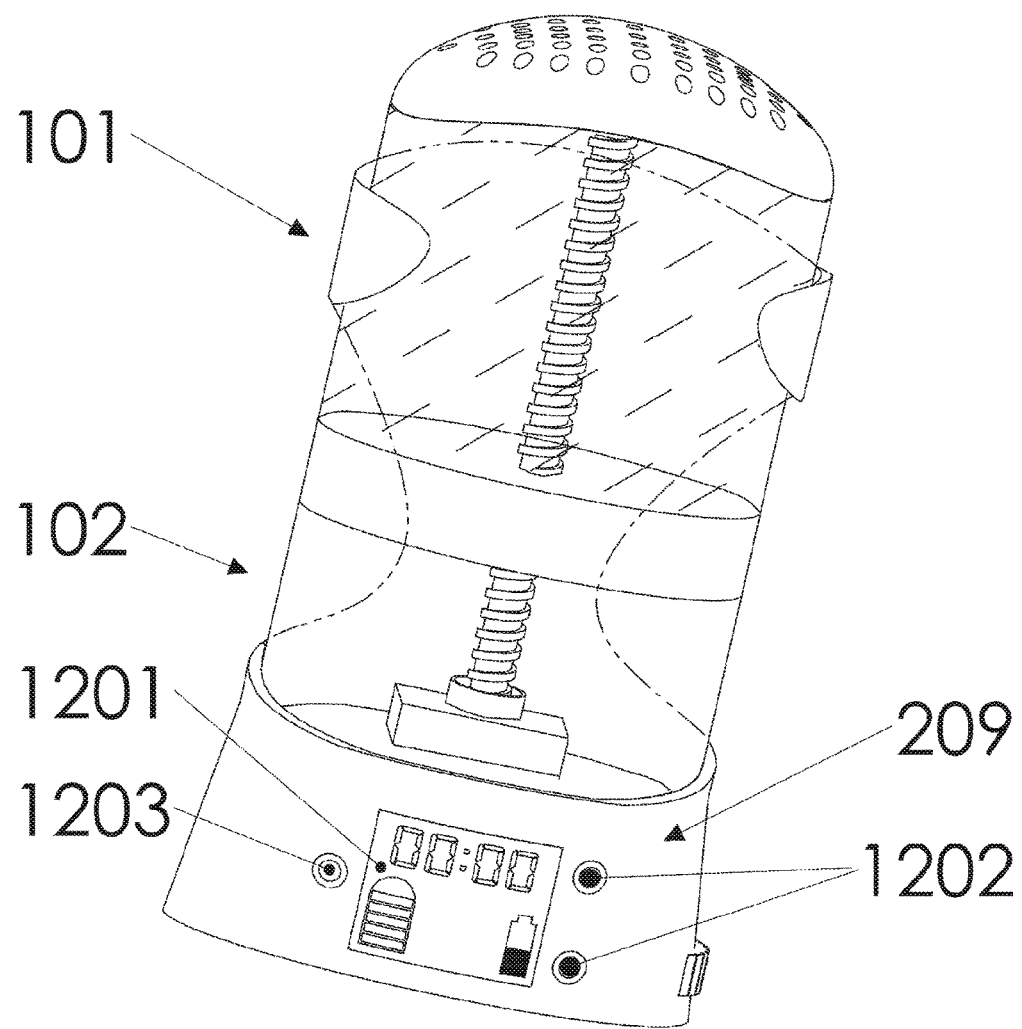
FIG. 12 illustrates a perspective front view of an embodiment comprising a digital display.

In an alternative embodiment, the container holder may comprise a digital display 1201 as shown in FIG. 12. The display 1201 may be located, for example, in the lower portion 209 of the container holder 101. Alternatively, the display 1201 may be located on any convenient part of the apparatus. The display 1201 may be powered by the power source 205 supplying power to the driving unit 201 (shown in FIG. 2) or by a separate power source. The electronic circuit that controls the display 1201 may be a separate entity or may be integrated in the electronic circuit 204 of the platform lifting mechanism (shown in FIG. 2). The digital display 1201 may be operative to indicate at least one parameter selected from the group consisting of: a remaining amount of the composition, a time the apparatus has last been used, remaining life of a battery coupled to the apparatus, current time, current date, and a remaining number of applications of the composition. Alternatively, an additional option may be incorporated in the display 1201, whereby the user sets an alarm as a reminder to use the apparatus. These are only examples of what the display might show. As known in the art some of these features include the use of one or more setting buttons 1202, which can be located anywhere on the apparatus. Also, optionally, one or more light indicators 1203 may replace or be incorporated with the digital display 1201, anywhere on the apparatus, to serve one or more of the functions presented above.

Figure 13A:
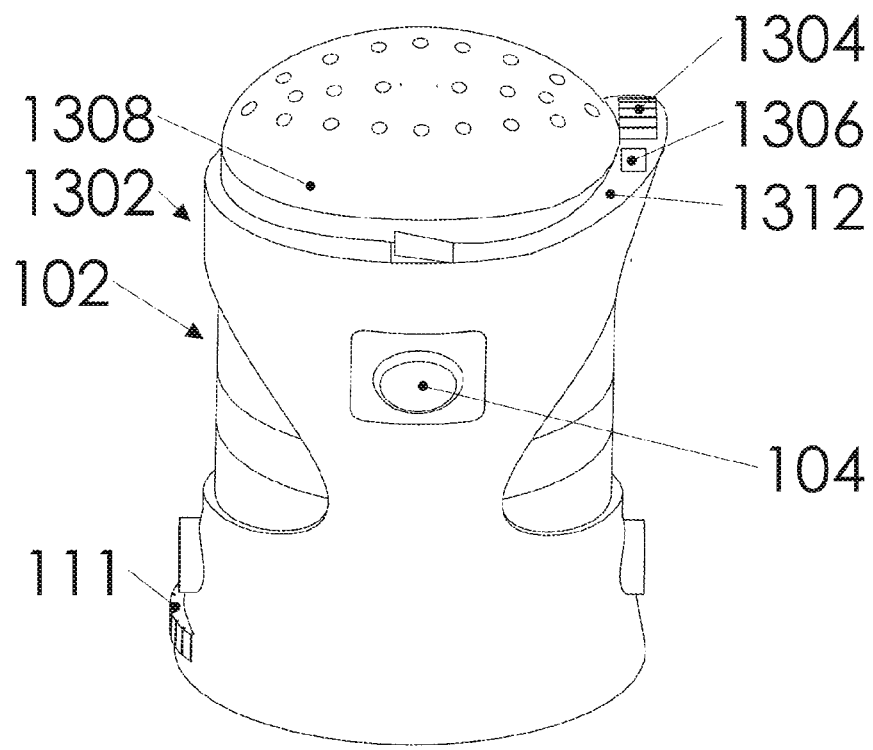
FIG. 13A shows an embodiment where the apparatus comprises an automatic dispensing mechanism.

In another embodiment shown in FIG. 13A, the apparatus comprises a mechanism that automatically dispenses the composition out of the container 102 when the user places the apparatus near or on the desired location of application. In this case, the apparatus comprises a detector 1306, configured to detect proximity or contact between an upper surface 1308 of the container 102 and skin of a subject. The detector 1306 may be coupled to an upper surface 1312 of the container holder 1302.

Figure 13B:
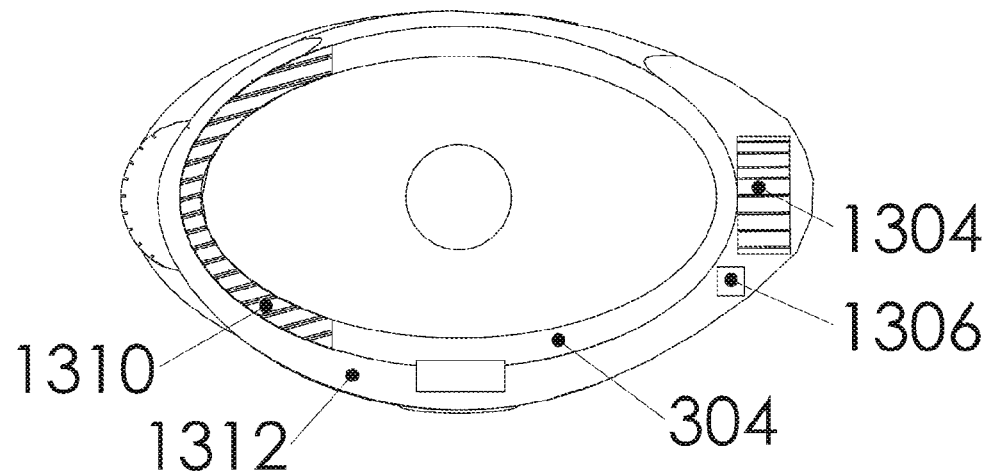
FIG. 13B presents a perspective upper view of the container holder of FIG. 13A.

An exemplary detector may comprise at least one detector selected from the group consisting of: a pressure sensor, a mechanical switch, and an optical proximity detector. FIG. 13B presents a perspective upper view of the container holder 1302. In this exemplary design, the detector may be configured to detect proximity between the upper surface of the container 1308 and the skin of the subject by detecting a force between the container 102 and the container holder 1302, using a force detector 1310 (shown as dashed lines representing plastic material). The force detector is located at the bottom of the cavity 304 where the container 102 sits when coupled to the container holder 1302. In one embodiment, the power source 205 is operative to inhibit driving of the driving unit 201 (shown in FIG. 2) in the absence of a detection of proximity by the detector 1306 or detector 1310, even in response to the actuation of the one or more user input elements 104, 501 or 502 (shown in FIG. 5). In another embodiment, the power source 205 is operative to facilitate driving of the driving unit 201 in response to the detection of proximity by the detector 1306 or detector 1310 or in response to the actuation of the one or more user input elements 104, 501 or 502. In yet another embodiment, the apparatus is configured to detect movement of the container 102 with respect to the skin, while the detector is in contact with skin. In this case, the detector may comprise a roller 1304 as shown in FIG. 13B. When the user slides the apparatus on the skin, the roller 1304 turns and activates the driving unit 201. The roller 1304 may control electric components that allow a preset amount to be dispensed per angular rotation of the roller 1304. In this case, the amount is typically equally dispensed over the area of application regardless of the speed of application. Alternatively, a combination of both a detector 1306 and a roller 1304 may be used. In this example, the user input element 104 may be included and the user may have the option of using the apparatus using the user input element 104 or the automatic dispensing option. Alternatively, the user input element 104 may be omitted. In addition, optionally, for a solid stick apparatus, the same automatic dispensing mechanism extrudes the stick out of the container and retracts it back also automatically. FIG. 13A and FIG. 13B present the detector 1306 and the roller 1304 located on the container holder 1302. Alternatively, the detector and the roller may be located on the upper surface 1308 of the container 102.

Figure 14A:
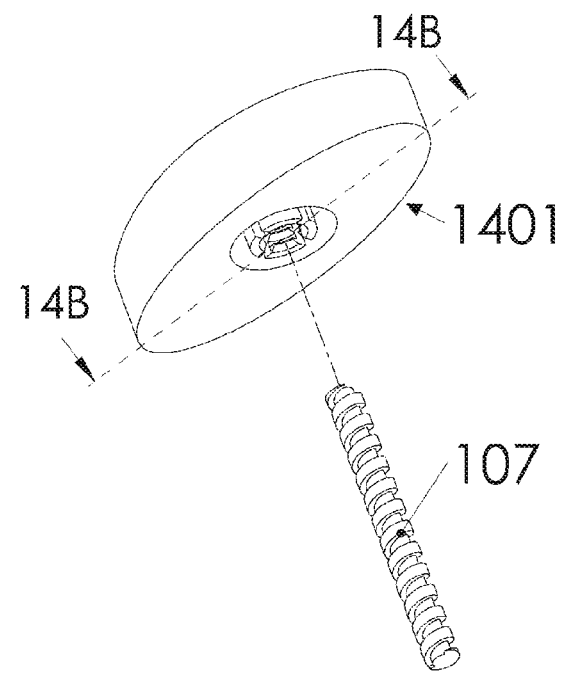
FIG. 14A shows a platform that allows insertion of the shaft in one direction without the need for rotation.
Figure 14B:
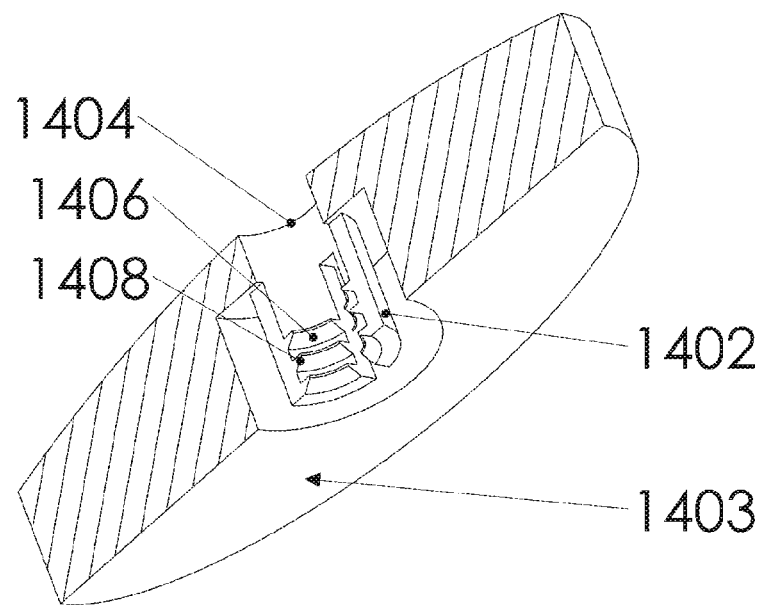
FIG. 14B shows a cross-sectional view of the platform of FIG. 14A.

FIG. 14A presents an embodiment where the platform 106 has been modified to be a movable platform 1401. In this embodiment, as can be seen in FIG. 14A, the threaded shaft 107 is insertable into the movable platform without rotation of the threaded shaft 107 with respect to the movable platform 1401. As shown in FIG. 14B, the movable platform 1401 comprises flexible threaded segments 1402 which surround a hole 1404 and which facilitate insertion of the threaded shaft 107 through the hole 1404, without rotation of the shaft 107, by bending away from an axis of the shaft 107 upon insertion of the shaft 107 through the hole 1404. In this design, the flexible segments 1402 are located on the bottom surface 1403. Following insertion of the shaft 107 through the hole 1404, the flexible threaded segments 1402 are configured to threadedly engage the threaded shaft 107. In this design, the threaded shaft 107 is removable from the platform 1401 by rotation, and removal of the threaded shaft 107 from the platform 1401 is inhibited in the absence of rotation of the threaded shaft 107 with respect to the platform 1401. The thread 1408 has a slope 1406 that allows sliding of the shaft in the desired direction.

FIG. 15 presents a platform 1405 that is similar to platform 1401 of FIG. 14A, except in that the flexible segments are located on the top surface 1407 of the platform. This design allows the shaft to slide with less force.

The platform design shown in FIG. 14A and FIG. 15 allows the container 102 to comprise a platform without a shaft as shown in FIG. 16B. FIG. 16A shows an embodiment where the lower portion 209 of the container holder 1501 comprises a threaded shaft 1502 fixedly coupled to the driving unit 201 without the need for a coupling mechanism 202 (shown in FIG. 2). This feature allows the container to be generally simple and cheap to manufacture. In this case, when the user attaches the container 102 to the container holder 1501, some force is applied against the platform, which might push the composition out. To inhibit this, the top surface may be sealed by the manufacturer with a removable seal. This feature is a common practice that also prevents the composition from drying. Also, in order to inhibit drying of the composition, the threaded hole 1404 (shown in FIG. 14B) may be sealed by the manufacturer prior to the shaft insertion. FIG. 16B presents a container 102 not comprising a shaft but comprising a platform 1405. When the container holder 1501 is coupled to the container 102, the threaded shaft 1502 is inserted into the movable platform 1405 of FIG. 15 of the container 102. To allow coupling between the container and the container holder, the container provides an opening for the shaft. In FIG. 16B, the container comprises an opening 1504 at the lower portion. The opening may vary for example from 25 to 0.06 cm2 (cross-sectional area of a relatively small shaft). In this case, the user may throw away (or recycle) the container 102 that includes the platform 1405 and reuse the container holder 1501 that includes the shaft 1502. In this embodiment, the disposable part is generally cheap to manufacture and easy to assemble. In order to allow easy release of the container 102 from the container holder 1501 when the threaded shaft 1502 is coupled to the platform 1405, the threaded shaft 1502 is gradually removable from the platform 1405 by rotation of the threaded shaft 1502 that is induced by the driving unit 201 during regular use of the apparatus. In this case, the threaded shaft is sized such that it is removed from the platform 1405 essentially upon completion of the composition in the container 102.

Figure 17:
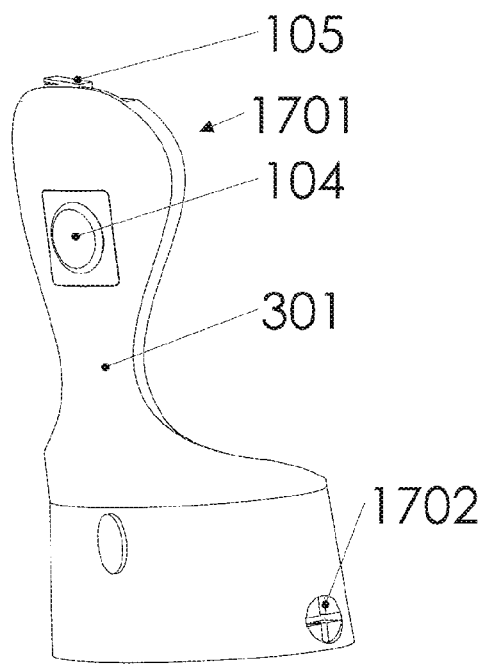
FIG. 17 shows an embodiment showing the container holder not comprising the grips and the wings.

FIG. 17 shows a different design 1701 of the container holder. In this design, the grips 306 and 308 and the wings 310 and 312 (shown in FIG. 3) are omitted. As can be seen, the container holder 1701 has the same spine design feature 301 which allows placement of the user input elements 104 and 105 in the desired location. All the features previously described may be included in the container holder 1701. In this exemplary embodiment (as well as in the other embodiments described herein), the quantity input element 1702 may be adjusted using a screwdriver (or another tool) to vary the amount of composition to be dispensed. In this case, the amount is preset by the manufacturer and if desired, the user may vary the amount using the screwdriver or other tool. Alternatively, the quantity input element 1702 may be incorporated inside the container holder 1701 and the user may not have direct access to change it.

Figure 18:
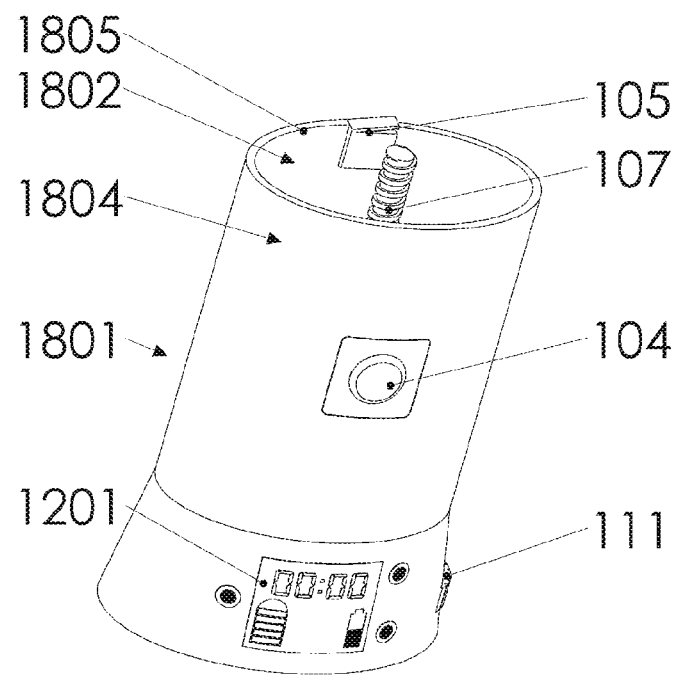
FIG. 18 shows an embodiment of a container holder where the upper portion of the container holder is shaped to define a closed shape. In this embodiment, the container holder also comprises a shaft that is fixedly coupled to the driving unit.

FIG. 18 presents an embodiment where the upper portion 1804 of the container holder 1801 is shaped to define a closed shape having an opening 1805 to receive the container 102. The closed shape is configured to completely surround at least a portion of the container 102. Optionally the container holder 1801 encloses the shaft 107 that is fixedly coupled to the driving unit. In this example, the container 102 may include a platform design as presented in FIG. 14 and FIG. 15 and may shaped to conform to the inner surface 1802 of the container holder 1801. This exemplary embodiment shows that the container holder is not restricted to a specific shape and can be implemented in any desired and convenient shape. This exemplary embodiment also allows the user input elements 104 and 105 to be placed in a convenient location on the container holder. This exemplary embodiment may include any of the features presented above, for example the digital display 1201, the amount adjusting knob 111, or any release mechanism presented in previous figures.

Figure 19:
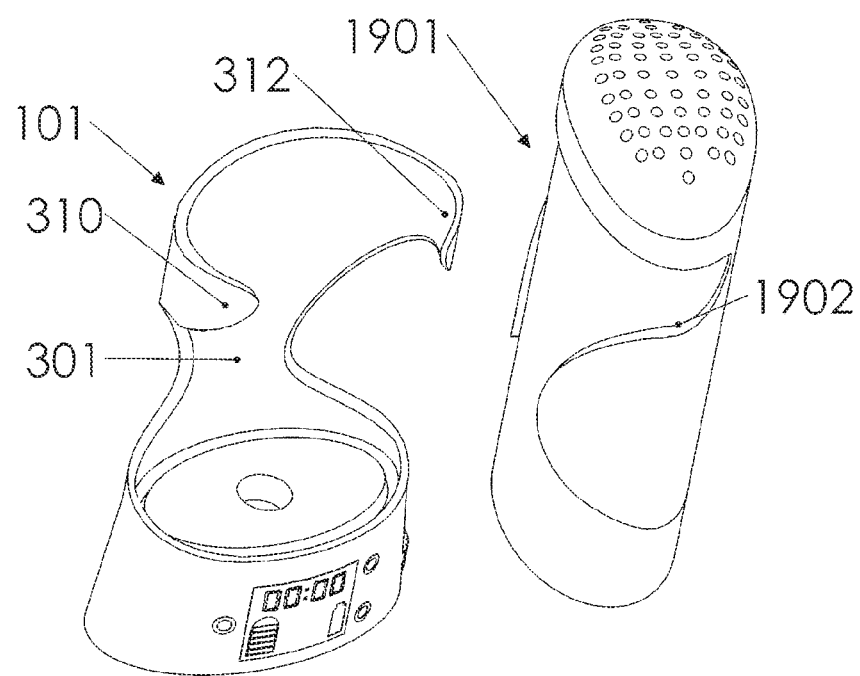
FIG. 19 shows an embodiment where the container is shaped with indents to complementarily fit the container holder.
Figure 20:
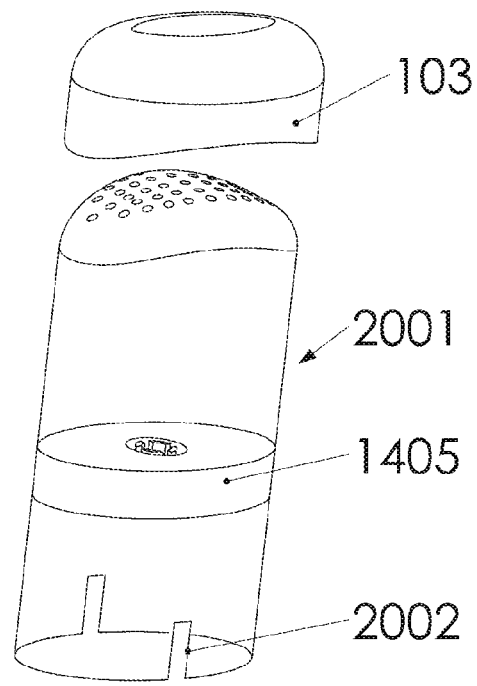
FIG. 20 shows a container where the lower surface is shaped to define a grooved surface.
Figure 21:
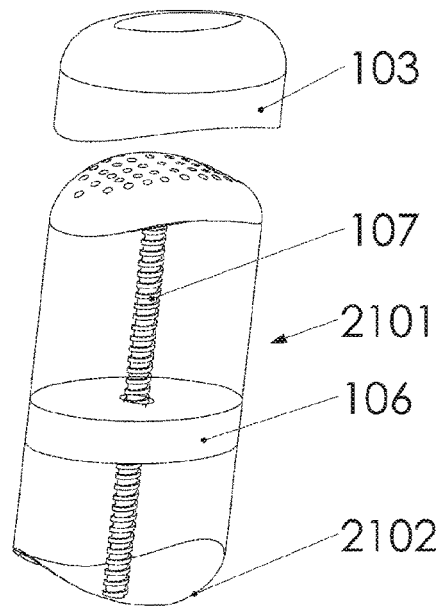
FIG. 21 shows a container where the lower surface is shaped to define a round convex surface.
Figure 22:
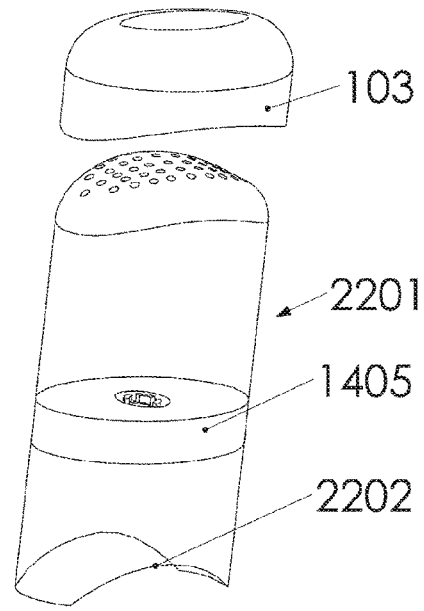
FIG. 22 shows a container where the lower surface is shaped to define a concave surface.
Figure 23:
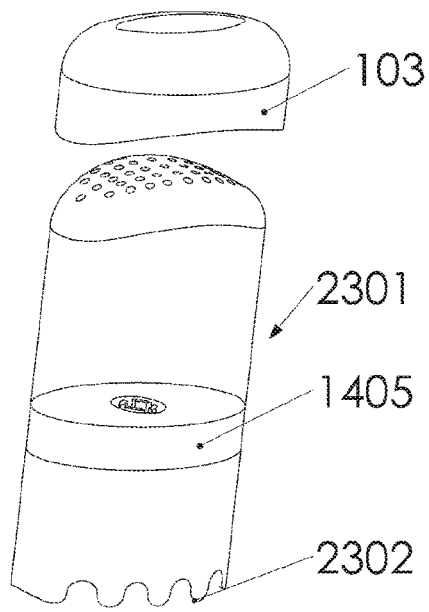
FIG. 23 shows a container where the lower surface is shaped to define a wavy surface.
Figure 24:
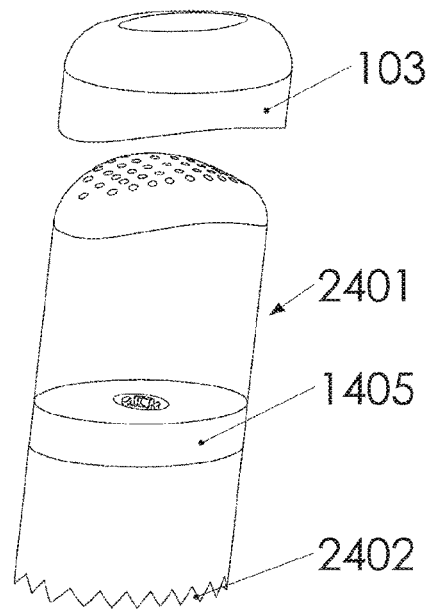
FIG. 24 shows a container where the lower surface is shaped to define a toothed surface.

FIG. 19 presents an embodiment where the external surface of the container 1901 is shaped to fit the container holder 101. Specifically the container 1901 comprises protrusions 1902 having a shape complementary to the shape of the spine 301 and wings 310 and 312. In this embodiment, when the container 1901 is coupled to the container holder 101, the apparatus forms a smooth and esthetic entity. For some applications, the complementary shapes serve as a locking/release mechanism that couples the container 1901 to the container holder 101.

FIG. 20, FIG. 21, FIG. 22, FIG. 23 and FIG. 24 show different containers (2001,2101,2201, 2301, and 2401, respectively) where the lower surface is shaped to define a grooved surface (2002 in FIG. 20), a round (convex) surface (2102 in FIG. 21), a concave surface (2202 in FIG. 22), a wavy surface (2302 in FIG. 23), or a toothed surface (2402 in FIG. 24) to correspond to a corresponding surface of the container holder. This feature provides that only a matching container can be used with a given container holder. A non-matching container and container holder do not couple properly. FIG. 20, FIG. 22, FIG. 23 and FIG. 24 comprise the platform 1405 of FIG. 15 without a shaft while FIG. 21 comprises the platform 106 with the shaft 107.

In the case where the apparatus comprises a container and a container holder (e.g. FIG. 1) which are not fixedly coupled as shown in FIG. 11, the consumer typically buys one container holder (e.g. FIG. 4A) and reuses it with a container (FIG. 4B). The container as packaged for sale typically comprises a composition, a movable platform (e.g. 106, 1401 or 1405) and it may or may not comprise a shaft (as shown in FIG. 4B, FIG. 20, FIG. 21, FIG. 22, FIG. 23 and FIG. 24). The container may be sold with a cap. The composition comprises at least one composition selected from the group consisting of: a deodorant, an antiperspirant, a skin-care composition, a pharmaceutical composition, a cosmetic composition, and an ultrasound gel composition. The platform is configured such that movement of the platform dispenses the composition from the container. The apparatus is packaged for sale to a consumer and does not comprise a shaft which by rotation thereof moves the platform up within the container. In the case where the container comprises a shaft (e.g. FIG. 4B), rotation of the shaft within the container does not move the platform and the user cannot use the container when it is not coupled to the container holder. The above also applies in cases where the container holder comprises a shaft and the container comprises the platform (e.g. FIG. 16A and FIG. 16B).

Figure 25:
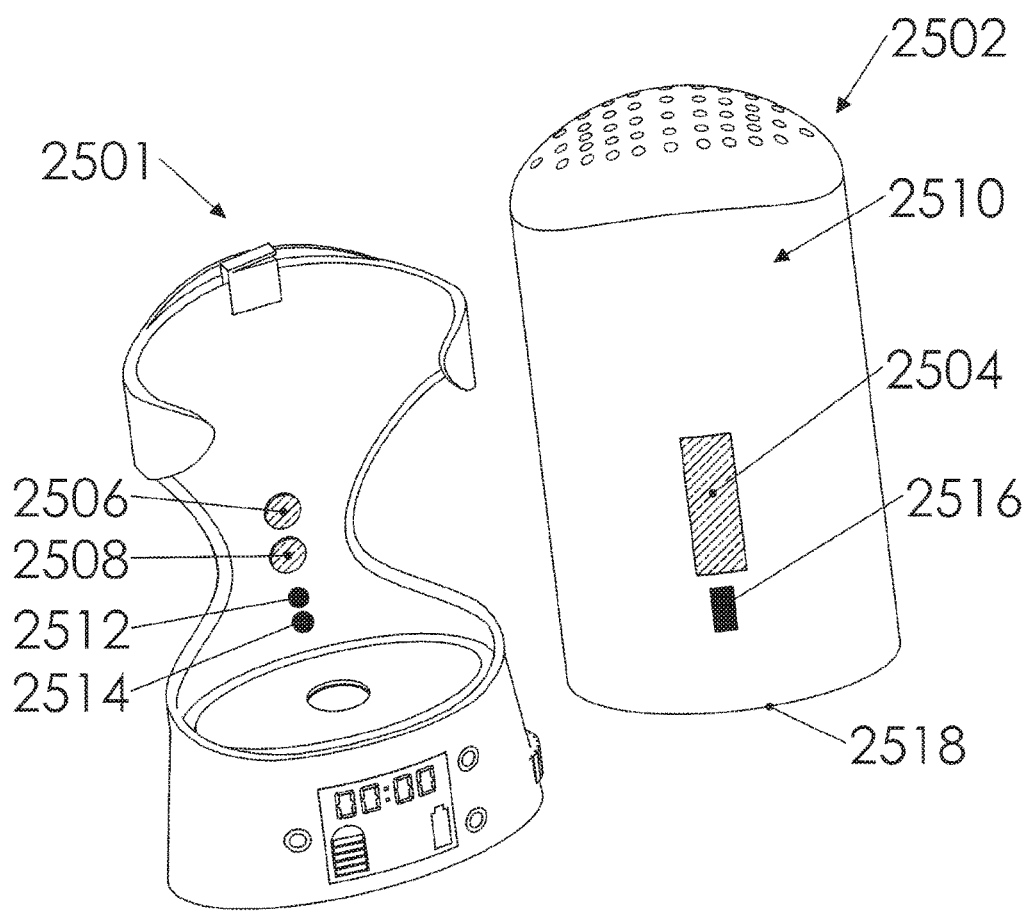
FIG. 25 shows an embodiment wherein the container holder comprises a coupling-detection element, configured to detect coupling of the container holder to the container.

FIG. 25 shows an embodiment wherein the container holder 2501 comprises a coupling-detection element, configured to detect coupling of the container holder to the container 2502. The coupling-detection element is configured to detect at least one parameter selected from the group consisting of: an electrical contact of the coupling-detection element with a conductive portion of the container, a magnetic coupling of a portion of the coupling-detection element with a corresponding portion of the container, and a level of reflection from a portion of the container. The detectable element may be disposed between 2 and 5 cm of a bottommost surface 2518 of the container 2502.

In the embodiment shown in FIG. 25, both the container 2502 and the container holder 2501 comprise an electrical element positioned such that upon coupling of the container 2502 to the container holder 2501, an electronic circuit is closed or an electric signal is transmitted, to allow detection of coupling between the container 2502 and the container holder 2501. Coupling detection can be achieved by closing a circuit using an electrically conductive element. In this case, the container 2502 may comprise an electrically conductive element 2504 disposed on an outer surface 2510 of the container 2502. The container holder 2501 may include an electronic circuit, and the electrically conductive element is positioned such that upon coupling of the container 2502 to the container holder 2501, the electrically conductive element 2504 closes the electronic circuit by bridging two or more points of the coupling-detection element 2506 and 2508. The size of the electrically conductive element may vary but in general it is within 1 cm to 5 cm in length. In another embodiment the electrically-conductive element may not be straight. Coupling detection can be achieved in various ways such as magnetic coupling, where a coupling-detection element 2512 may be located on the container holder 2501 and a magnetic coupling portion 2516 may be located on the container 2502. Alternatively an optical measure of level of reflection may be used; in this case the coupling-detection element may comprise a photo-emitter and a photodetector 2514. The coupling-detection element is configured to detect level of reflection from a portion 2516 of the container. These are only examples and coupling detection can be done in various ways. Coupling detection may serve different purposes such as allowing activation of the driving unit upon actuation of one or more user-input elements while inhibiting driving of the driving unit in the absence of a detection; it may also serve to indicate that the container 2502 is properly coupled to the container holder 2501. The coupling-detection element may be configured to detect a predefined shape characteristic of a portion of the container, and to inhibit driving of the driving unit in the absence of a detection of the predefined shape as shown in FIG. 26 and FIG. 27.

Figure 26:
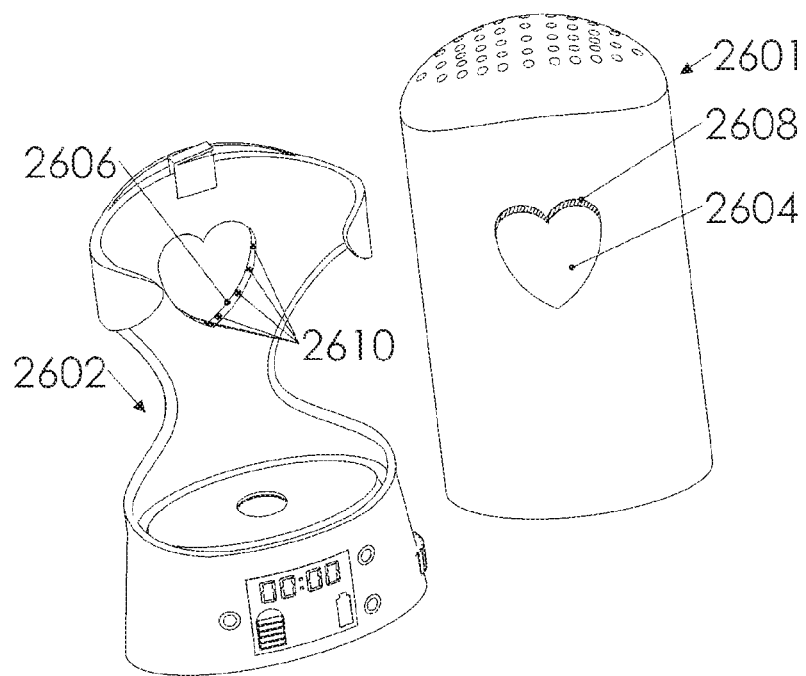
FIG. 26 shows an embodiment where the container and the container holder comprise complementary shapes. In this embodiment, the container is shaped to define a protrusion and the container holder comprises an indent.

FIG. 26 shows an embodiment wherein a portion of the container 2601 is shaped to define a predefined surface shape 2604 configured to couple to a corresponding predefined surface shape 2606 of the container holder 2602, and configured to inhibit slipping of the container from the container holder. As can be seen in the figure, the predefined surface shapes on the container 2601 and the container holder 2602 comprise complementary shapes 2604 and 2606, respectively. In this embodiment, the predefined surface shapes are shaped to define a protrusion 2604 on the container 2601 and an indent 2606 on the container holder 2602. But in other embodiments, the predefined surface shapes may be shaped to define an indent on the container and a protrusion on the container holder. This feature provides that a matching container and container holder are used. A non-matching container and container holder do not couple properly and the container may slip from the container holder in the absence of a surface shape. Moreover, the predefined surface shapes may serve as a locking/release mechanism that couples the container to the container holder. The depth of the indent 2606 may be smaller than the thickness of the container holder surface. Alternatively, the indent may penetrate the whole thickness and therefore create a hole in the container holder 2602. In this case, in order to release the container 2601 from the container holder 2602, the user may simply press on the protrusion 2604 through the hole formed by the indent 2606. Also, in this case, the shape of the protrusion 2604 is visible on the outer surface of the container holder 2602 when the container is coupled to the container holder. This embodiment shows a coupling-detection element 2610 that is configured to detect the predefined shape characteristic 2604 by assessing an electrical current that is changed by coupling of the portion of the container 2601 having the predefined shape characteristic 2606 to the container holder 2602. Change in electric current can be from a zero current to a non-zero current, from non-zero current to zero current or change to a permitted level of current. In this embodiment, protrusion 2604 may include an electrically-conductive element 2608 that upon coupling to the container holder 2602 creates contact among two or more points of the coupling detection element 2610 (black dots in the figure). In this figure, the complementary shapes form a heart shape but in other embodiments, they can comprise any shape. For example, they can comprise a word and/or a trademark logo as shown in FIG. 27.

Figure 27:
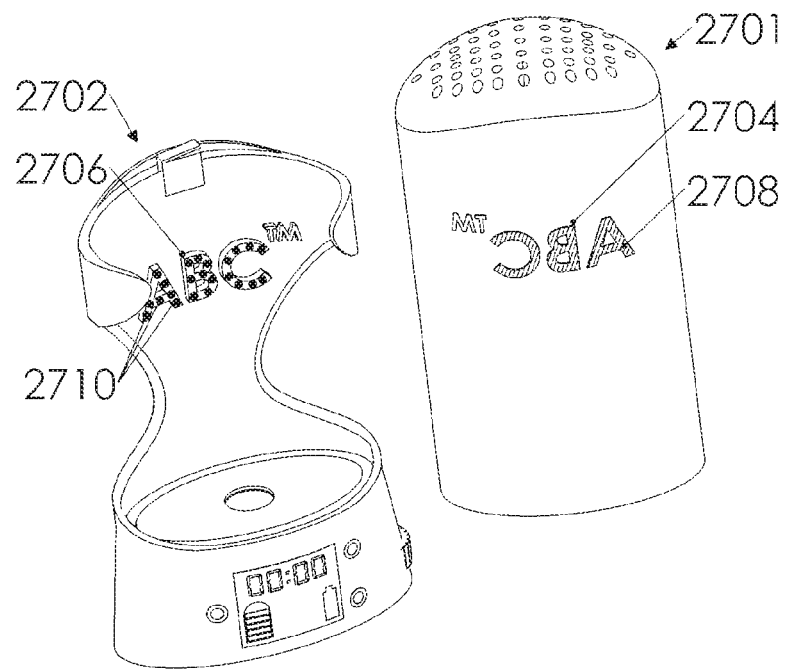
FIG. 27 shows an embodiment where the container and the container holder comprise complementary shapes. In this embodiment, the container is shaped to define an indent and the container holder comprises a protrusion.

FIG. 27 presents a similar embodiment to the one presented in FIG. 26, wherein a portion of the container 2701 is shaped to define a predefined surface shape 2704 configured to couple to a corresponding predefined surface shape 2706 of the container holder 2702, and configured to inhibit slipping of the container from the container holder. As can be seen in the figure, the predefined surface shapes on the container 2701 and the container holder 2702 comprise complementary shapes 2704 and 2706, respectively. In this embodiment, the predefined surface shapes comprise a protrusion 2706 on the container holder 2702 and an indent 2704 on the container 2701. This feature provides that a matching container and container holder are used. A nonmatching container and container holder do not couple properly and the container may slip from the container holder in the absence of a surface shape. Moreover, the predefined surface shapes may serve as a locking/release mechanism that couples the container 2701 to the container holder 2702. This embodiment shows a coupling-detection element 2710 that is configured to detect the predefined shape characteristic 2704 by assessing an electrical current that is changed by coupling of the portion of the container 2701 having the predefined shape characteristic 2704 to the container holder 2702. The predefined shape 2704 of the container 2701 is configured to fit a complementary shape 2706 on the container holder 2702. In this embodiment, indent 2704 may include an electrically-conductive element 2708 that upon coupling to the container holder forms a contact among the different points of the coupling-detection element 2710 (black dots in the figure). In this figure, the complementary shapes form a trademark logo but in other embodiments, they can comprise any shape.

Figure 28:
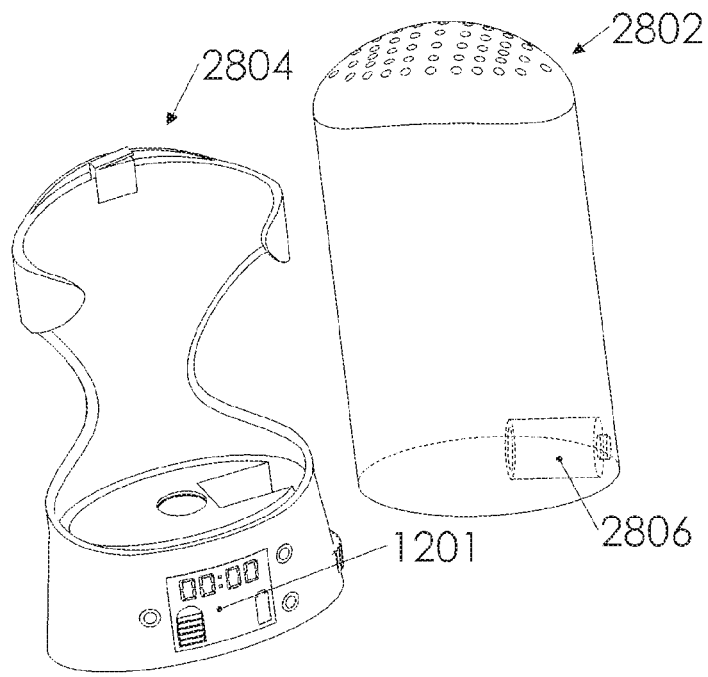
FIG. 28 shows an embodiment where the container comprises one or more batteries, which upon coupling to the container holder provides power to the driving unit.

FIG. 28 shows an embodiment where the container 2802 comprises one or more batteries 2806 (shown in phantom), which upon coupling to the container holder 2804 provide power to the container holder which can serve to power the driving unit, or any other electrical component. This feature can eliminate the need for the user to replace batteries since upon completion of the composition the user loads a new container 2802 that comprises new batteries 2806. A new battery holds enough power to drive the driving unit for the desired number of applications. For simplicity, FIG. 28 does not show a platform in the container but a typical container comprises a platform and may comprise a shaft. In this embodiment, the container holder has no power source to drive the driving unit and therefore cannot be used with a container without a power source. The container holder might have a power source to provide power to other components such as the digital display 1201.

Figure 29:
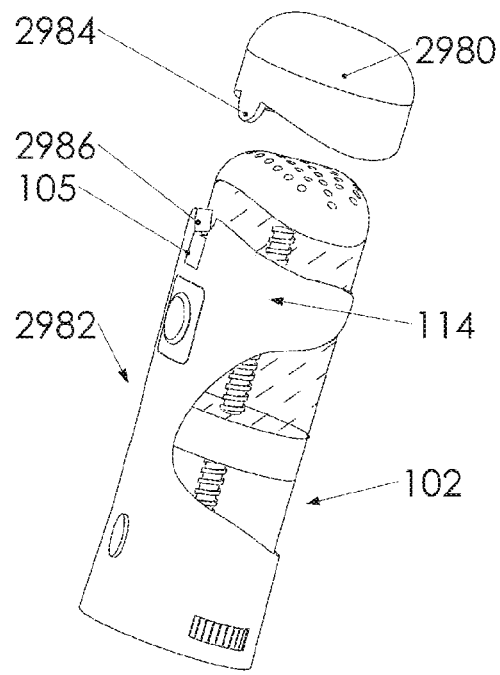
FIG. 29 shows an embodiment where the cap has a lower surface shaped to define a protrusion which is of complementary shape to an indent located on the upper portion of the container holder.

FIG. 29 shows an embodiment comprising a cap 2980 removably placeable on the container 102. The cap has a lower surface that is shaped to define a protrusion 2984. The protrusion 2984 is of complementary shape to the indent 2986 located on the upper portion 114 of the container holder 2982. In another embodiment, the indent may be in the cap while the complementary protrusion is located on the upper surface of the container holder. For symmetry purposes, the cap 2980 may have two protrusions or two indents on opposite sides. In this embodiment, the apparatus is for use with a container holder having a switch 105, where the protrusion or the indent are configured to activate the switch 105 upon coupling of the cap 2980 to the container 102 when the container holder 2982 is also coupled to the container 102.

Figure 30:
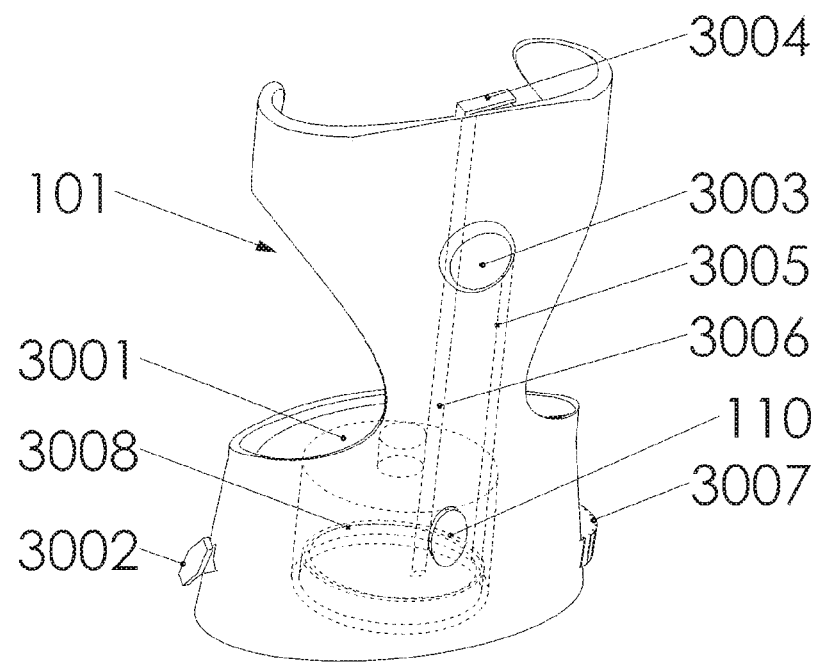
FIG. 30 presents another embodiment where the apparatus comprises a non-electromechanical driving unit and non-electronic user input elements.

FIG. 30 presents another embodiment where the apparatus comprises a non-electromechanical driving unit 3001 and non-electronic user input elements 3002, 3003, 3004 and 3007. In this embodiment, the driving unit 3001 comprises a spring-based driving unit and the user input elements 3002, 3003 and 3004 comprise mechanical user input elements. This embodiment may include any of the features described above, mutatis mutandis. In this embodiment, the container holder 101 comprises a driving unit 3001 powered by a spring 3008 and a knob 3002 configured to facilitate winding of the spring 3008. An activation user input element 3003 may be located anywhere on the apparatus and can communicate with the driving unit 3001 via a rod 3005 that may be inserted into the body of the container holder 101. The activation user input element 3003 may serve to actuate the driving unit 3001. The spring-loaded driving unit 3001 may be implemented such that each activation causes a predetermined angular rotation, as is apparent to those skilled in the art having read the specification of the present patent application. This feature allows a generally predetermined and repeatable amount of composition to be dispensed during each operation, which amount is set using the knob 3007. The mechanical user input element 3004 comprises a switch and serves to prevent accidental activation of the driving unit 3001. The switch 3004 mechanically communicates with the driving unit 3001 for example through a rod 3006, which may be inserted into the body of the container holder 101. In addition to the spring-loaded drive mechanism, an electric power source may be used for operation of features such as the display or an alarm, described above.

Figure 31:
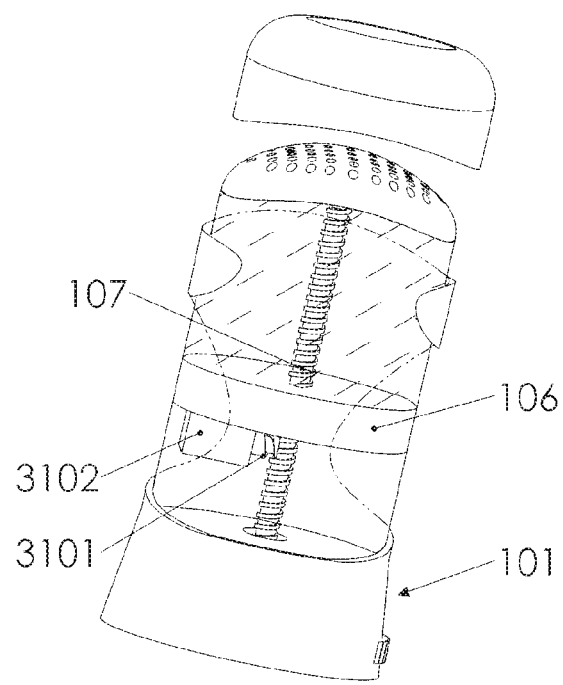
FIG. 31 shows a perspective front view of an embodiment where the driving unit is attached to the platform.

In another embodiment shown in FIG. 31, the driving unit 3102 may be integrated to the platform 106 and connected to the shaft 107 through a coupling 3101 instead of being located in the lower portion 209 of the container holder 101 as described in previous embodiments.

Figure 32:
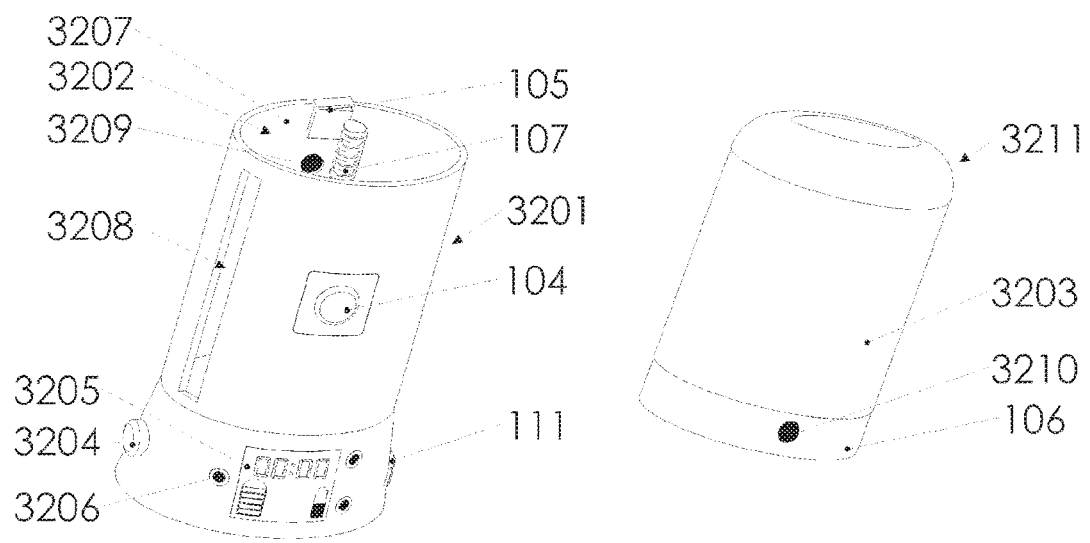
FIG. 32 shows an embodiment for use with a solid stick composition where the container and the container holder are fixedly coupled.

Another embodiment is shown in FIG. 32 where the apparatus is for use with a solid stick 3211. In this design, the container and the container holder are fixedly coupled, forming one entity 3201. Similar to the embodiment shown in FIG. 5, the apparatus is shaped to have an open upper surface 3202 suitable for facilitating passage of the solid stick 3211. The direction selection user input element 3204 is configured to set the direction of rotation of the driving unit 201 (shown in FIG. 2) in response to actuation of the user input element 104 and hence the direction of the platform 106 movement. Therefore, actuation of the user input element 104 may move the platform 106 upward or downward depending on the position of the user input element 3204. When the solid stick composition 3203 is finished, the user can simply refill the apparatus 3201 with a new solid stick 3211. A new solid stick typically comprises the composition 3203 attached to a platform 106. Refill is typically done by inserting the new solid stick 3211 into the apparatus 3201 through the upper surface 3202, and then retracting the platform and the composition into the apparatus by pressing the user input element 104. In this case, the user input element 104 is set to move the platform downward through the user input element 3204. This refill is simple to the user and also allows the manufacturer of the apparatus to produce refills at a cheaper price with easier and environmentally-friendly manufacturing. In other embodiments, the user input element 104 may be replaced by a user input element, further comprising two user input elements 501 and 504 as shown in FIG. 5. In this case, the direction selection user input element 3204 is omitted. In response to actuation of the second user input element 504, the driving unit 201 is configured to move the platform 106 in a direction that is opposite to the direction in which the driving unit 201 is configured to move the platform 106 in response to actuation of the first user input element 501.

The apparatus may also include a level indication element, which is arranged to indicate a remaining amount of the composition and, for example, signal the user when the composition is about to end. The level indication element may be selected from the group consisting of: an electrically-conductive element, a magnetic element and an optically-reflective element. In some embodiments, the level indication element may comprise a level-sensing element 3209 that may be positioned on the inner surface 3207 of the apparatus 3201 such that when the platform 106 reaches a predefined level, the user will receive an indication that the composition is about to end. The level-sensing element 3209 may be configured to detect the platform 106. Level-sensing can be achieved in various ways such as magnetic detection, where a level-sensing element 3209 may be located on the inner surface 3207 of the apparatus 3201 and a magnetic sensing portion 3210 may be located on the platform 106. Alternatively an optical measure of level of reflection may be used; in this case the level-sensing element may comprise a photo-emitter and a photodetector, where the level-sensing element 3209 is configured to detect level of reflection from a portion 3210 of the container. These are only examples and level-sensing can be done in various ways. The level indication element may be configured to indicate a continuously-variable remaining amount of the composition, which may be achieved, for example, using a linear encoder or any other continuous level detection technique. The level indication described above may be included in all the embodiments previously described.

The level indication element may comprise an indication light source 3206, configured to indicate the remaining amount of the composition. The light source may comprise a light emitting diode (LED) or any other light source. The light source may be configured to be activated permanently once the platform reached the predefined level or may be activated only upon removal of the cap. The light source 3206 may be located on the lower portion of the apparatus 3201, as shown in FIG. 32 or in any other location. In some embodiments, the light source may be configured to indicate the remaining amount of the composition by flashing or changing color, and may be activated when the platform reaches the predetermined level.

Figure 33:
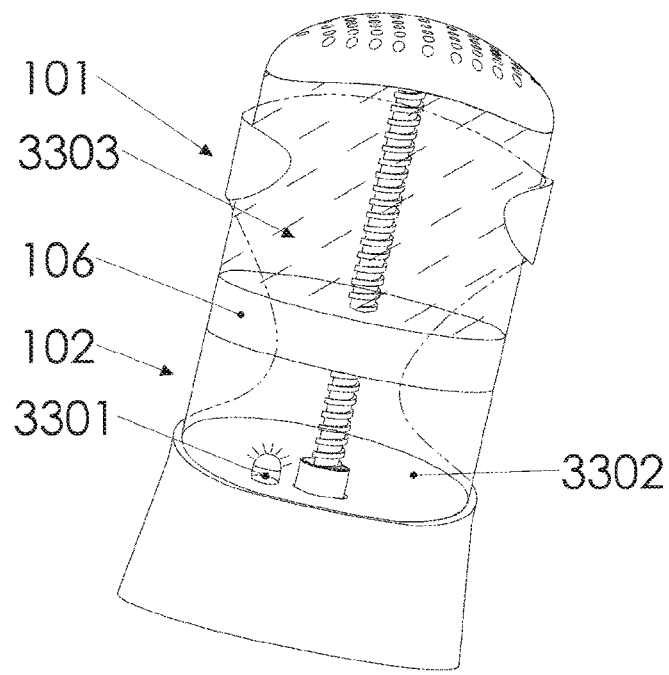
FIG. 33 shows a perspective front view of an embodiment where the apparatus comprises a light source.

In other embodiments, the indication may be a warning shown on the digital display 3205 or a vibration resulting from the operation of a vibrating element 3401 (shown in FIG. 34) when the predetermined level is reached. In other embodiments, the light source can be located in a way that signals the user when the composition is about to end, for example when the light source becomes visible to the user through the remaining amount of composition. This can be achieved by placing the light source 3206 on the upper surface of the platform. It may also be placed inside the apparatus 3201 as shown in FIG. 33. In this case, a transparent platform 106 may be used. In yet other embodiments, the level indication element is shaped to define a transparent slot 3208 in the container that may be located on a side surface of the apparatus 3201 or in any other convenient location. In other embodiments, the level indication element is shaped to define a transparent slot in the container holder 3201.

The transparent slot 3208 shows the solid stick composition 3203 and clearly shows when the composition is about to end just due to its transparency or for example through a light source located inside the apparatus.

FIG. 33 shows an embodiment where the composition is a gel and where the apparatus is for use with a container, and wherein the apparatus comprises a light source 3301 that may comprise a light emitting diode (LED) or any other light source. The light source may be positioned anywhere in the apparatus and may vary in type. In this exemplary embodiment, the light source 3301, which may be an LED for example, is configured to illuminate the composition 3303 in the container, showing clearly the amount of composition remaining (since the composition is typically transparent). The light source may be on the upper part of the platform 106, on the upper surface 3302 of the lower portion of the container holder 101, or any other convenient location. In other embodiment, the light source 3301 may be located inside the lower part of the container holder 101 where it serves to illuminate the perimeter of the container 102. This design also serves as a way to illuminate the composition 3303. In other embodiments, the light source is configured to be activated when a cap of the container is removed or upon actuation of one or more user input elements. In embodiments where the switch 105 (shown in FIG. 1) is included, the light is also an indication that the cap is properly closed and therefore the light turns off when the cap is properly placed and may help in preventing drying of the composition and accidental operation of the device. In other embodiments, the light may be operated when the user presses the user input element 104. When the light source 3301 is placed inside the apparatus, it may serve a dual function: showing the remaining amount of composition 3303 and indicating if the cap is properly closed. In other embodiments, the light source 3301 may serve to light up a digital display, making it easier for the user to read the indication displayed. Also, the light source 3301 may vary in color, indicating the level of battery life. For example, it may vary from green when the battery is fully charged to red when it's about to be empty. In other embodiments, the light source may vary in color indication the amount of composition remaining.

Figure 34:
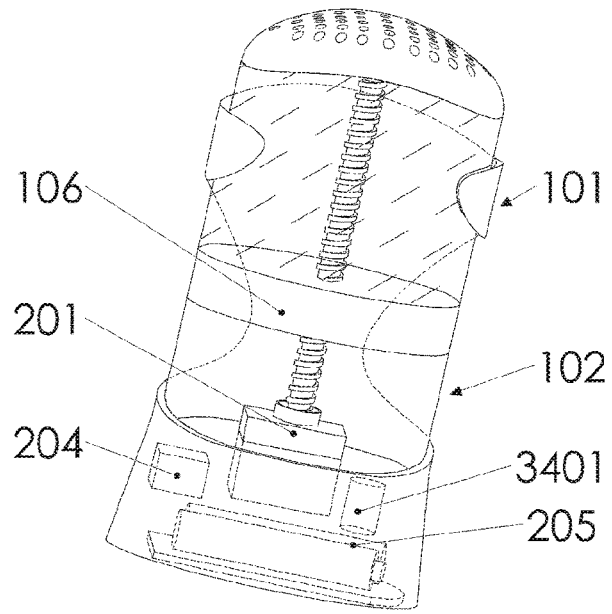
FIG. 34 shows a perspective front view of an embodiment where the apparatus comprises a vibration element.

In the exemplary embodiment shown in FIG. 34, the apparatus comprises a vibration element 3401. The vibration may serve different functions and may also be configured to operate in several ways. In some embodiments, the vibration element 3401 may be configured to be activated upon coupling of the container 102 to the container holder 101. Moreover, the vibrations may be produced only if a matching container 102 is coupled to the container holder 101. The vibration element 3401 may be powered by the batteries 205 and configured through the electronic circuit 204. In other embodiments, the vibration element 3401 may be configured to be activated upon actuation of the one or more user input elements (e.g. 104). This may serve to evenly spread the composition and/or to massage the armpit. In other embodiments, the vibration may serve to better infuse the composition into the area of application. This feature is frequently relevant in the case where the composition comprises a skin-care or cosmetic composition such as an anti-aging cream. Optionally, the vibration may be produced for an amount of time longer than the time needed for the predetermined amount to be dispensed. This may give the user the option to massage the armpit or any other skin area for a desired amount of time. In this case, when the user actuates the user input element 104, the composition is extruded for a predetermined amount of time while the vibration element 3401 is activated as long as the user input element 104 is actuated, and therefore producing vibrations for as long as desired. In other embodiments, the vibration element 3401 may be configured to be activated when a cap of the container (example, 103) is removed.

Figure 35:
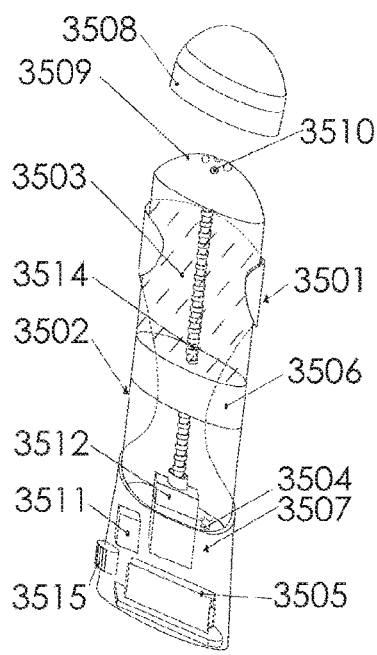
FIG. 35 shows an embodiment of a different shape.

FIG. 35 schematically illustrates a perspective view of the apparatus comprising the same features and functionality shown in previous embodiments, but in a different shape. The apparatus comprises a container holder 3501 and is for use with a container 3502 containing a composition 3503 selected from the group consisting of: a deodorant, an antiperspirant, a skin-care composition, a composition including a pharmaceutical composition, a cosmetic composition, and an ultrasound gel composition. The skin-care composition may comprise, for example, a face cream. Alternatively, the skin-care or cosmetic composition may comprise an anti-aging cream, an eye cream, a cleanser, a moisturizer cream, a concealer, a liquid foundation, an acne treatment, a body lotion, a sunscreen, a lip gloss, or another composition. In some embodiments, the composition comprises a pharmaceutical composition. For example, the pharmaceutical composition may include a hormone. The hormone may include a steroid hormone, e.g., testosterone. In other applications, the hormone may include cortisone or any other type of hormones. In other embodiments, the composition 3503 comprises a pharmaceutical composition such as diclofenac (Voltaren™) gel; methyl salicylate, menthol, camphor, and/or triethanolamine salicylate (Bengay™ or Icy Hot™, Mebo™, a pressure sore treatment, or another composition. In the embodiment shown in FIG. 35, the apparatus includes a movable platform 3506. The container holder 3501 comprises a lower portion 3507 comprising a driving unit 3512 and a power source 3505, and the power source 3505 is operative to drive the driving unit 3512 to rotate the shaft 3514 to move the movable platform 3506 of the container 3502, in response to actuation of the one or more user input elements (104 and 105 (FIG. 1), for example). When the one or more user input elements are actuated, the composition is dispensed through the holes 3510, which in this embodiment are shaped and sized facilitate applications directed to small areas such as eye creams, acne treatment and others. In this case, the upper surface 3509 may have a surface area of 0.03 cm2 to 3.5 cm2. The driving unit 3512 may be configured to operate for a predetermined amount of time, therefore dispensing a preset amount of composition 3503 at each use. The predetermined amount of composition is desired in many applications such as eye creams or acne treatment and others, where typically a small, predetermined amount is needed. This feature may be useful in other applications as well, such as pharmaceutical applications including a hormone such as testosterone where the accuracy of the amount used at each application is desired. The predetermined amount of the composition may be set by the user using a user input element such as a switch/knob 3515, or alternatively may be preset by the manufacturer. The apparatus may comprise a light source 3504 such as an LED. The light source 3504 may be positioned anywhere in the apparatus and may also not be an LED. It may be positioned in such a way as to illuminate all of the composition, to clearly show the amount of composition remaining. The light source may be on the upper part of the platform 3506, on the lower portion 3507 of the container holder 3501 or any other convenient location. The light source may be activated when the cap 3508 is removed or when the driving unit 3512 is operated. The holes 3510 may be configured to dispense any of the compositions listed above and may be arranged in any size and distribution according to the specific application. In some embodiments where the composition comprises an eye cream for example, the upper surface 3509 may be configured to fit the shape of the eye contour. In other embodiments, the upper surface may be shaped for a relatively small area of application (for example, acne treatment). In some embodiments, the apparatus comprises a vibration element 3511 (e.g., as described hereinabove), configured to massage the area where the composition 3503 is applied. In other embodiments, the vibration element 3511 is configured such that the vibration frequency is suitable to effectively infuse the composition to the skin. This feature may be included in applications where the composition comprises a skin-care or cosmetic composition, for example anti-aging cream, where the vibration may help to enhance the efficacy and/or uptake of the composition in use.

Figure 36:
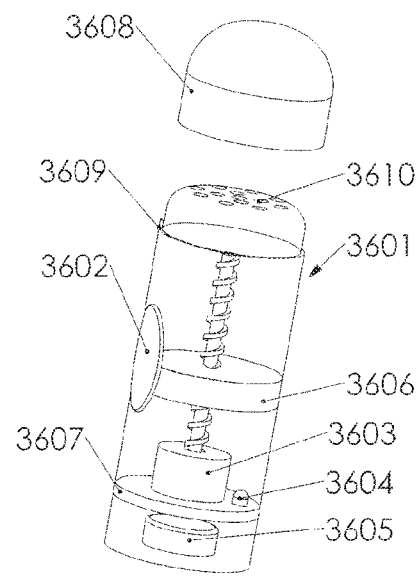
FIG. 36 shows an embodiment of yet another shape and where the container holder and the container are fixedly coupled.

FIG. 36 schematically illustrates a perspective view of the apparatus 3601, where the container and the container holder are fixedly coupled to each other. The apparatus comprises a driving unit 3603 and a power source 3605 operative to drive the driving unit to move the movable platform 3606, in response to actuation of the user input element 3602. The composition is dispensed through the holes 3610. The driving unit 3603 may be configured to operate for a predetermined amount of time. The apparatus 3601 may comprise a light source 3604 such as an LED. The light source may be on the upper part of the platform 3606, on the base 3607 or any other convenient location. Some embodiments as shown in this figure may include a switch 3609 configured to activate the light source when the cap 3608 is removed and to deactivate it when the cap is placed. In this case, proper placement of the cap deactivates the light and serves as an indication to the user that the cap is properly placed. This may inhibit the composition from drying or being damaged by being exposed to air. In other embodiments where the composition comprises a pharmaceutical product (for example, a composition including a hormone such as testosterone, estrogen, progesterone, DHEA and others), this feature increases the likelihood that the composition is securely stored, and inhibits spill and undesirable contact with the composition.

It should be noted that the holes from which the composition is extruded as presented in all the exemplary embodiments shown in the previous figures might vary in size according to the viscosity of the composition.

Additionally, in an exemplary embodiment, the apparatus may be equipped with a way to signal to the user that the platform lifting mechanism has been operated. For example, this may comprise only the sound produced by the operation of the driving unit 201. Alternatively, it may be an audible signal or vibration.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for use with a container that contains a composition, the container including a movable platform, the apparatus comprising:
   a container holder comprising:
   an upper portion, which comprises one or more user input elements; and
   a lower portion comprising (a) a driving unit, which comprises an electric motor, and (b) a power source, wherein the power source is operative to drive the driving unit to move the movable platform of the container, in response to actuation of the one or more user input elements,
   wherein the container holder comprises a user-activatable release mechanism operative to release the container from the container holder,
   wherein the user-activatable release mechanism comprises an energy-storage element, which is configured to store energy by deformation thereof, upon initial coupling of the container to the container holder, and which is configured to release the stored energy during the coupling of the container to the container holder, prior to actuation of the user-activatable release mechanism, and
   wherein the container holder is operative to become locked to the container by means of the release of the stored energy during the coupling of the container to the container holder, prior to actuation of the user-activatable release mechanism.

2. The apparatus according to claim 1, wherein the composition is selected from the group consisting of: a skin-care composition, a composition including a pharmaceutical composition, a cosmetic composition, and an ultrasound gel composition, and wherein the apparatus is for use with the container containing the selected composition.

3. The apparatus according to claim 2, wherein the selected composition includes the pharmaceutical composition, and wherein the apparatus is for use with the container containing the pharmaceutical composition.

4. The apparatus according to claim 1,
wherein the container holder comprises a coupling-detection element, configured to detect coupling of the container holder to the container, and
wherein the coupling-detection element is configured to detect a predefined shape characteristic of a portion of the container, and to inhibit driving of the driving unit in the absence of a detection of the predefined shape.

5. The apparatus according to claim 1,
wherein the container holder comprises a coupling-detection element, configured to detect coupling of the container holder to the container, and
wherein the coupling-detection element is configured to detect at least one parameter selected from the group consisting of:
electrical contact of the coupling-detection element with a conductive portion of the container,
magnetic coupling of a portion of the coupling-detection element with a corresponding portion of the container, and
a level of reflection from a portion of the container.

6. The apparatus according to claim 1, wherein the one or more user input elements are configured to be placed in a vicinity of an upper 75% of the container, when the container is coupled to the container holder.

7. The apparatus according to claim 1, wherein the upper portion is shaped to define a container-coupling upper portion, configured to couple the upper portion of the holder to sides of the container.

8. The apparatus according to claim 7, wherein the container-coupling upper portion comprises one or more grips which are configured to hold an upper portion of the container.

9. The apparatus according to claim 7, wherein the container-coupling upper portion comprises exactly two wings which are configured to hold an upper portion of the container.

10. The apparatus according to claim 9, wherein the two wings are configured to simultaneously apply a pressing force to the container.

11. The apparatus according to claim 1, wherein the upper portion is shaped to define a spine, extending up from the lower portion.

12. The apparatus according to claim 1,
wherein the upper portion is shaped to define a spine, extending up from the lower portion, and
wherein the upper portion is shaped to define at least one shape selected from the group consisting of:
one or more grips extending from the spine, the one or more grips being configured to prevent the spine from bending by holding the spine in contact with the container, and
a closed shape having an opening therein, which closed shape is configured to completely surround at least a portion of the container.

13. The apparatus according to claim 1, wherein the upper portion of the container holder comprises a switch, which is configured to disable functioning of the driving unit when a cap of the container is disposed on the container, and wherein the switch is configured to not disable functioning of the driving unit when the cap of the container is not disposed on the container.

14. The apparatus according to claim 1, wherein the lower portion comprises a threaded shaft fixedly coupled to the driving unit, the threaded shaft being insertable into the movable platform of the container without rotation of the threaded shaft with respect to the movable platform.

15. Apparatus for use with a container that contains a composition, the container including a movable platform, the apparatus comprising:
a container holder comprising:
an upper portion, which comprises one or more user input elements; and
a lower portion comprising (a) a driving unit, which comprises an electric motor, and (b) a power source, wherein the power source is operative to drive the driving unit to move the movable platform of the container, in response to actuation of the one or more user input elements,
wherein the lower portion comprises a threaded shaft fixedly coupled to the driving unit, the threaded shaft being insertable into the movable platform of the container without rotation of the threaded shaft with respect to the movable platform, and
wherein the threaded shaft is removable from the movable platform by rotation, and wherein removal of the threaded shaft from the movable platform is inhibited in the absence of rotation of the threaded shaft with respect to the movable platform.

16. The apparatus according to claim 15, wherein the composition is selected from the group consisting of: a skin-care composition, a composition including a pharmaceutical composition, a cosmetic composition, and an ultrasound gel composition, and wherein the apparatus is for use with the container containing the selected composition, and wherein the apparatus is for use with the container containing the selected composition.

17. The apparatus according to claim 16, wherein the selected composition includes the pharmaceutical composition, and wherein the apparatus is for use with the container containing the pharmaceutical composition.

18. Apparatus for use with a container that contains a composition, the container including a movable platform, the apparatus comprising:
a container holder comprising:
an upper portion, which comprises one or more user input elements; and
a lower portion comprising (a) a driving unit, which comprises an electric motor, and (b) a power source, wherein the power source is operative to drive the driving unit to move the movable platform of the container, in response to actuation of the one or more user input elements,
wherein the container holder further comprises a detector, configured to detect a parameter selected from the group consisting of: (a) proximity between an upper surface of the container and skin of a subject, and (b) contact between an upper surface of the container and skin of a subject, and
wherein the power source is operative to facilitate driving of the driving unit in response to the detection by the detector.

19. The apparatus according to claim 18, wherein the power source is operative to inhibit driving of the driving unit in the absence of a detection of proximity by the detector, even in response to the actuation of the one or more user input elements.

20. The apparatus according to claim 18, wherein the detector is coupled to an upper surface of the container holder.

21. The apparatus according to claim 18, wherein the detector comprises an optical proximity detector.

22. The apparatus according to claim 18, wherein the detector comprises a mechanical detector.

23. The apparatus according to claim 22, wherein the mechanical detector comprises at least one mechanical detector selected from the group consisting of: a pressure sensor and a mechanical switch.

24. The apparatus according to claim 22, wherein the mechanical detector is configured to detect the proximity between the upper surface of the container and the skin of the subject by detecting a force between the container and the container holder.

25. The apparatus according to claim 18, wherein the detector is configured to detect movement of the container with respect to the skin, while the detector is in contact with the skin.

26. The apparatus according to claim 1, wherein the container holder is fixedly coupled to the container.

27. The apparatus according to claim 18, wherein the composition is selected from the group consisting of: a skin-care composition, a composition including a pharmaceutical composition, a cosmetic composition, and an ultrasound gel composition, and wherein the apparatus is for use with the container containing the selected composition, and wherein the apparatus is for use with the container containing the selected composition.

28. The apparatus according to claim 27, wherein the selected composition includes the pharmaceutical composition, and wherein the apparatus is for use with the container containing the pharmaceutical composition.

29. Apparatus comprising:
a composition; and
a container that contains the composition, the container comprising a movable platform configured such that movement of the platform dispenses the composition from the container,
the apparatus being packaged for sale to a consumer and not comprising a shaft which by rotation thereof moves the platform up within the container,
further comprising a shaft threadedly engaged to the platform in a manner such that rotation of the shaft moves the shaft within the container while not moving the platform up within the container.

30. The apparatus according to claim 29, wherein the composition is selected from the group consisting of: a skin-care composition, a composition comprising a pharmaceutical composition, a cosmetic composition, and an ultrasound gel composition.

31. The apparatus according to claim 30, wherein the selected composition comprises the pharmaceutical composition.

32. The apparatus according to claim 29, wherein the apparatus is characterized in that downward motion of the shaft within the container is not restricted during rotation of the shaft, but if downward motion of the shaft within the container were to be restricted during rotation of the shaft, then rotation of the shaft in one direction would move the platform up within the container.

33. The apparatus according to claim 29, wherein the apparatus as packaged for sale to the consumer comprises a battery that is disposable within the container, the battery not being configured to supply electricity to any component of the apparatus that (a) is included in the apparatus as packaged for sale to the consumer and (b) may drive the movable platform.

34. The apparatus according to claim 29, wherein the apparatus is for use with a container holder, and wherein a portion of the container is shaped to define a predefined surface shape configured to couple to a corresponding predefined surface shape of the container holder, and configured to inhibit slipping of the container from the container holder.

35. Apparatus comprising:
a composition; and
a container that contains the composition, the container comprising a movable platform configured such that movement of the platform dispenses the composition from the container,
the apparatus being packaged for sale to a consumer and not comprising a shaft which by rotation thereof moves the platform up within the container,
wherein the movable platform is not threadedly coupled to a shaft,
wherein the movable platform is shaped to define a hole,
wherein the apparatus is for use with a threaded shaft, and
wherein the movable platform comprises flexible threaded segments which surround the hole and which facilitate insertion of the threaded shaft through the hole, without rotation of the shaft, by bending away from an axis of the shaft upon insertion of the shaft through the threaded hole.

36. The apparatus according to claim 35, wherein, following insertion of the shaft through the threaded hole, the flexible threaded segments are configured to threadedly engage the threaded shaft.

37. The apparatus according to claim 35, wherein the composition is selected from the group consisting of: a skin-care composition, a composition including a pharmaceutical composition, a cosmetic composition, and an ultrasound gel composition, and wherein the apparatus is for use with the container containing the selected composition.

38. The apparatus according to claim 37, wherein the selected composition comprises the pharmaceutical composition.

39. Apparatus comprising:
a composition; and
a container that contains the composition, the container comprising a movable platform configured such that movement of the platform dispenses the composition from the container,
the apparatus being packaged for sale to a consumer and not comprising a shaft which by rotation thereof moves the platform up within the container,
wherein the container comprises a detectable element disposed between 2 and 5 cm of a bottom-most surface of the container, the detectable element being selected from the group consisting of: an electrically-conductive element, a magnetic element, and an optically-reflective element.

40. The apparatus according to claim 39, wherein the composition is selected from the group consisting of: a skin-care composition, a composition including a pharmaceutical composition, a cosmetic composition, and an ultrasound gel composition, and wherein the apparatus is for use with the container containing the selected composition.

41. The apparatus according to claim 40, wherein the selected composition comprises the pharmaceutical composition.

42. Apparatus comprising:
- a composition; and
- a container that contains the composition, the container comprising a movable platform configured such that movement of the platform dispenses the composition from the container,
- the apparatus being packaged for sale to a consumer and not comprising a shaft which by rotation thereof moves the platform up within the container,
- wherein the container comprises a detectable element disposed between 2 and 5 cm of an upper-most surface of the container, the detectable element being selected from the group consisting of: an electrically-conductive element, a magnetic element, and an optically-reflective element.

43. The apparatus according to claim 42, wherein the composition is selected from the group consisting of: a skin-care composition, a composition including a pharmaceutical composition, a cosmetic composition, and an ultrasound gel composition, and wherein the apparatus is for use with the container containing the selected composition.

44. The apparatus according to claim 43, wherein the selected composition comprises the pharmaceutical composition.

* * * * *